(12) United States Patent
Zhang et al.

(10) Patent No.: US 12,378,529 B2
(45) Date of Patent: Aug. 5, 2025

(54) METHOD FOR CULTURING COLORECTAL CANCER SOLID TUMOR PRIMARY CELLS AND COLORECTAL CANCER ASCITES PRIMARY TUMOR CELLS AND SUPPORTING REAGENTS

(71) Applicant: GENEX HEALTH CO., LTD, Beijing (CN)

(72) Inventors: Hanshuo Zhang, Beijing (CN); Shenyi Yin, Beijing (CN)

(73) Assignee: GENEX HEALTH CO., LTD, Beijing (CN)

( * ) Notice: Subject to any disclaimer, the term of this patent is extended or adjusted under 35 U.S.C. 154(b) by 909 days.

(21) Appl. No.: 17/251,537

(22) PCT Filed: Aug. 5, 2019

(86) PCT No.: PCT/CN2019/099245
§ 371 (c)(1),
(2) Date: Jun. 8, 2021

(87) PCT Pub. No.: WO2019/238143
PCT Pub. Date: Dec. 19, 2019

(65) Prior Publication Data
US 2021/0284970 A1 Sep. 16, 2021

(51) Int. Cl.
*C12N 5/09* (2010.01)

(52) U.S. Cl.
CPC ........ *C12N 5/0693* (2013.01); *C12N 2500/00* (2013.01); *C12N 2500/02* (2013.01); *C12N 2500/32* (2013.01); *C12N 2500/38* (2013.01); *C12N 2500/60* (2013.01); *C12N 2500/90* (2013.01); *C12N 2501/11* (2013.01); *C12N 2501/115* (2013.01); *C12N 2501/12* (2013.01); *C12N 2501/15* (2013.01); *C12N 2501/30* (2013.01); *C12N 2501/40* (2013.01); *C12N 2501/415* (2013.01); *C12N 2501/727* (2013.01); *C12N 2509/00* (2013.01)

(58) Field of Classification Search
CPC ............. C12N 5/0693; C12N 2500/00; C12N 2500/02; C12N 2500/32; C12N 2500/38; C12N 2500/60; C12N 2500/90; C12N 2501/11; C12N 2501/115; C12N 2501/12; C12N 2501/15; C12N 2501/30; C12N 2501/40; C12N 2501/415; C12N 2501/727; C12N 2509/00
See application file for complete search history.

(56) References Cited

U.S. PATENT DOCUMENTS

| | | | | |
|---|---|---|---|---|
| 7,932,084 B2 * | 4/2011 | Katz | ..................... | C12N 5/0667 435/325 |
| 2007/0292389 A1 * | 12/2007 | Stassi | ....................... | A61P 35/00 435/375 |

FOREIGN PATENT DOCUMENTS

| | | | |
|---|---|---|---|
| CN | 101984051 A | 3/2011 | |
| CN | 102439135 A | 5/2012 | |
| CN | 103468746 A | 12/2013 | |
| CN | 103865876 A | 6/2014 | |
| CN | 104024401 A | 9/2014 | |
| CN | 105154405 A | 12/2015 | |
| CN | 105647870 A | 6/2016 | |
| CN | 105754933 A | 7/2016 | |
| CN | 105907706 A | 8/2016 | |
| CN | 106190980 A | 12/2016 | |
| CN | 106479891 A | 3/2017 | |
| CN | 107094752 A | 8/2017 | |
| CN | 107794243 A | 3/2018 | |
| CN | 108070561 A | 5/2018 | |
| CN | 108148811 A | 6/2018 | |
| WO | 2007117565 A2 | 10/2007 | |
| WO | 2012168930 A2 | 12/2012 | |
| WO | WO-2017127921 A1 * | 8/2017 | ............ C12M 27/02 |
| WO | 2017156341 A1 | 9/2017 | |

OTHER PUBLICATIONS

Smith, M. L., et al., "The effect of non-steroidal anti-inflammatory drugs on human colorectal cancer cells: evidence of different mechanisms of action," European Journal of Cancer 36(5): 664-667. doi: 10.1016/s0959-8049(99)00333-0. (Year: 2000).*
Goodyear, A. W., et al., "Optimization of murine small intestine leukocyte isolation for global immune phenotype analysis," J Immunol Methods 405: 97-108. doi: 10.1016/j.jim.2014.01.014. (Year: 2014).*
Singh SR, Rameshwar P, editors. Somatic stem cells: methods and protocols. Clifton, NJ, USA: Humana Press; 2012. (Year: 2012).*
First Office Action issued in corresponding Chinese Application No. 201810607216.2; mailed Oct. 12, 2020; State Intellectual Property Office of the P.R. China, Beijing, China, 19 pgs.

(Continued)

*Primary Examiner* — Tracy Vivlemore
*Assistant Examiner* — Eric J Rogers
(74) *Attorney, Agent, or Firm* — HAUPTMAN HAM, LLP

(57) ABSTRACT

A method for culturing colorectal cancer solid tumor primary cells and colorectal cancer ascites primary tumor cells and supporting reagents. A method for culturing colorectal cancer solid tumor primary cells and colorectal cancer ascites primary cells and supporting reagents. Colorectal cancer solid tumor tissues are treated with mild cell dissociation reagents, and colorectal cancer cells are isolated from ascites with a mild method, thereby ensuring the vitality of cancer cells to the greatest extent. A special serum-free medium is prepared, and colorectal cancer solid tumor-derived tumor cells are cultured in vitro with a suspension culture system to ensure normal expansion of the cancer cells while eliminating the interference of normal cells to the greatest extent. The colorectal cancer primary cell culture obtained by the method are usable for in vitro experiments, second-generation sequencing, building of animal models, and building of cell lines at multiple cell levels.

17 Claims, 6 Drawing Sheets

(56) References Cited

OTHER PUBLICATIONS

First Office Action issued in corresponding Chinese Application No. 201810607219.6; mailed Sep. 27, 2020; State Intellectual Property Office of the P.R. China, Beijing, China, 25 pgs.
First Office Action issued in corresponding Chinese Application No. 201810607714.7; mailed Apr. 15, 2020; State Intellectual Property Office of the P.R. China, Beijing, China, 25 pgs.
First Office Action issued in corresponding Chinese Application No. 201810607728.9; mailed Oct. 26, 2020; State Intellectual Property Office of the P.R. China, Beijing, China, 17 pgs.
International Search Report issued in corresponding International Application No. PCT/CN2019/099245; mailed Nov. 8, 2019; State Intellectual Property Office of the P.R. China, Beijing, China, 8 pgs.
Guidelines for Clinical Drug Use of Common Diseases (Western Medicine), Threshold et al., Henan Science and Technology Publishing House, pp. 86-87, Mar. 31, 2017.
"Tumor Bioimmunotargeted Therapy", Han Baohui et al., p. 66, line 10, Shanghai Science and Technology Publishing House, Jun. 2006.
Encyclopedia of Chinese Medicine, Editorial Board of Encyclopedia of Chinese Medicine, p. 137, Shanghai Science and Technology Publishing House, Nov. 1986.
"Practical Medical Cell Culture Techniques", Wu Yanfeng et al., p. 493, last line—p. 494, line 7, Sun Yat-sen University Press, Jan. 2010.

\* cited by examiner

METHOD FOR CULTURING COLORECTAL CANCER SOLID TUMOR PRIMARY CELLS AND COLORECTAL CANCER ASCITES PRIMARY TUMOR CELLS AND SUPPORTING REAGENTS

RELATED APPLICATIONS

The present application is a National Phase of International Application Number PCT/CN2019/099245 filed Aug. 5, 2019 and claims priority to Chinese Application Numbers CN 201810607216.2 filed Jun. 13, 2018, CN 201810607728.9 filed Jun. 13, 2018, CN 201810607714.7 filed Jun. 13, 2018, and CN 201810607219.6 filed Jun. 13, 2018.

TECHNICAL FIELD

The present invention relates to the field of biotechnology, and specifically, to a method for culturing colorectal cancer solid tumor primary cells and colorectal cancer ascites primary tumor cells and supporting reagents.

BACKGROUND ART

Colorectal cancer is one of the most common malignant tumors that seriously threaten human health. The incidence of colorectal cancer in China is 9.24%, which occupies forth among all the malignant tumors. The mortality of colorectal cancer is 11.77%, which occupies fifth among all the malignant tumors. With economic development, improvement of living standards and changes in lifestyle, the incidence of colorectal cancer continues to rise. In addition, the colorectal cancer has a high risk of recurrence and metastasis. More than 50% of colorectal cancer patients experience varying degrees of recurrence and metastasis within months to years after radical treatment.

Although scientific research and medical institutions around the world have invested heavily in the research on the cause and development of colorectal cancer, people still know little about this disease. The colorectal cancer is a complex disease. Its occurrence and development are a dynamic process, involve the interaction of many signaling molecules that form a complex molecular regulatory network, and are also affected by external environmental factors. The cause and development process of colorectal cancer have strong individual differences and cannot be generalized. Therefore, it is a trend in the field of colorectal cancer research and even the field of colorectal cancer diagnosis and treatment to use primary cell cultures of colorectal cancer solid tumors as models for individualized and accurate research.

For advanced colorectal cancer patients who miss the operation opportunity, chemotherapy and targeted therapy are the most important treatment methods. The selection of the medication regimen for the first chemotherapy for newly treated patients is particularly important for the control of the patient's condition. With the widespread application of second-generation sequencing technology, through individualized gene sequencing and data mining, potentially effective drugs can be found by predicting sequencing results for only 30%-50% of colorectal cancer patients, and these medication regimens cannot be ensured to be able to effectively kill cancer cells in actual chemotherapy.

Traditional methods use colorectal cancer cell lines as colorectal cancer research models, which cannot represent the truth of cancer cells in thousands of different colorectal cancer patients and have great limitations. A Patient-Derived Xenograft (PDX) model, which represents the concept of precision medicine, cannot overcome the shortcoming that the modeling cycle is too long to guide clinical treatment. Medium-term and advanced colorectal cancer patients often have ascites that need to be excreted in time. Therefore, the ascites is a readily obtainable clinical sample, and shed colorectal cancer cells can often be found in the ascites. It is a trend in the field of colorectal cancer research and even the field of colorectal cancer diagnosis and treatment to use primary cell cultures of colorectal cancer solid tumors and primary tumor cell cultures of colorectal cancer ascites as models for individualized precision research.

The existing primary tumor cell culture technologies mainly include 2D culture. 3D culture, and reprogramming culture. These methods all face the problems of extremely long culture cycle, low culture success rate, and difficult removal of parenchyma cells to varying degrees.

SUMMARY OF THE INVENTION

In order to effectively solve the above technical problems, the present invention provides a novel culture technology and supporting reagents for colorectal cancer solid tumor primary cells and colorectal cancer ascites primary tumor cells. The core of this technology is: (1) colorectal cancer solid tumor tissues are treated with mild cell dissociation reagents to ensure the vitality of cancer cells in the tissues to the greatest extent; and (2) a special serum-free medium is prepared, and colorectal cancer solid tumor-derived tumor cells and colorectal cancer ascites primary tumor cells are cultured in vitro with a suspension culture system to ensure normal expansion of the cancer cells while eliminating the interference of normal cells to the greatest extent.

In the first aspect, the present invention claims a medium for culturing colorectal cancer primary cells.

A medium for culturing colorectal cancer primary cells according to the present invention consists of a ternary antibacterial and antifungal agent (penicillin-streptomycin-amphotericin B), HEPES, GLUTAMAX™, a human recombinant protein EGF, a human recombinant protein bFGF, a human recombinant protein HGF, a human recombinant protein Wnt-3a, a human recombinant protein Noggin. SB202190) (4-(4-fluorophenyl)-2-(4-hydroxyphenyl)-5-(4-pyridyl)-1H-imidazole). A83-01 (3-(6-Methyl-2-pyridinyl)-N-phenyl-4-(4-quinolinyl)-1H-pyrazole-1-carbothioamide). PRIMOCIN™. N-acetyl-L-cysteine. Nicotinamide, N-2 Supplement, cortisol. B27. ITS-X (Insulin. Transferrin, Selenium, Ethanolamine Solution), Y-27632 and an Advanced DMEM/F12 medium. A final concentration of penicillin in the ternary antibacterial and antifungal agent is 100-200 U/mL (such as 100 w/mL): a final concentration of streptomycin in the ternary antibacterial and antifungal agent is 100-200 µg/mL (such as 100 µg/mL): a final concentration of amphotericin B in the ternary antibacterial and antifungal agent is 100-250 ng/ml (such as 250 ng/mL): a final concentration of the HEPES is 8-12 mM (such as 10 mM): a final concentration of the GLUTAMAX™ is 0).8-1.2% (such as 1%. % represents a volume percentage); a final concentration of the human recombinant protein EGF is 10-100 ng/ml (such as 20 ng/ml or 40 ng/mL): a final concentration of the human recombinant protein bFGF is 10-50 ng/ml (such as 20 ng/ml); a final concentration of the human recombinant protein HGF is 5-25 ng/mL (such as 20 ng/ml); a final concentration of the human recombinant protein Wnt-3a is 200-300 ng/ml (such as 300 ng/mL); a final concentration of the human recombinant protein Noggin is 100-200 ng/ml (such as 150 ng/ml); a final concentration of the SB202190 is 5-10 μM (such as 10 μM); a final concentration of the A83-01 is 0.25-1.25 μM (such as 0.5 μM or 1 μM); a final concentration of the PRIMOCIN™ is 1% (volume percentage): a final concentration of the N-acetyl-L-cysteine is 0.5-2 mM (such as 1 mM): a final concentration of the Nicotinamide is 5-10 mM (such as 10 mM); a final concentration of the N-2 Supplement is 1% (volume percentage); a final concentration of the cortisol is 20-50 ng/ml (such as 20 ng/ml): a final concentration of the B27 is 1.5-2.5% (such as 2%, % represents a volume percentage); a final concentration of the ITS-X is 0.8-1.2% (such as 1%, % represents a volume percentage): a final concentration of the Y-27632 is 5-20 μM (such as 5 μM or 10 μM); and the balance is the Advanced DMEM/F12 medium.

Further, the composition of the ternary antibacterial and antifungal agent (penicillin-streptomycin-amphotericin B) is as follows: each milliliter contains 10,000 units of penicillin (base), 10,000 μg of streptomycin (base) and 25 μg of amphotericin B. The ternary antibacterial and antifungal agent (penicillin-streptomycin-amphotericin B) is "Antibiotic-Antimycotic, 100X" (such as GIBCO® #15240062, or other products with the same composition). Each milliliter of the "Antibiotic-Antimycotic, 100X" contains 10,000 units of penicillin (base), 10,000 μg of streptomycin (base) and 25 μg of amphotericin B, and penicillin G (sodium salt), streptomycin sulfate and amphotericin B in the form of 0.85% salt solutions are used as Fungizone® antifungal agents. The GLUTAMAX™ is a "glutamine supplemental solution comprising 200 mM L-alanyl-L-glutamine" (such as GIBCO® #35050061, or other products with the same composition). The composition of the "GLUTAMAX™ Supplement" is L-alanyl-L-glutamine, which is a substitute for L-glutamine, with a concentration of 200 nM and a solvent of 0.85% NaCl solution. The PRIMOCIN™ is an antibacterial agent (such as Invivogene #ant-pm-1, or other products with the same composition) for culturing primary cells, which is an antibiotic for protecting the primary cells from microbial contamination, has killing effects on gram-positive bacteria, gram-negative bacteria, *mycoplasma* and fungi, and comprises four antibiotics targeting DNA gyrase, prokaryotic ribosomal subunits, and ergosterol. The N-2 Supplement is "N-2 Supplement (100X)" (such as GIBCO® #17502001, or other products with the same composition such as Bottenstein's N2 formulation) providing a media supplemental formulation comprising insulin, transferrin, progesterone, putrescine, and selenium. The "N-2 Supplement (100X)" contains Human Transferrin (Holo) with a final concentration of 1 mM, 500 mg/L Insulin Recombinant Full Chain, 0.63 mg/L Progesterone, 10 mM Putrescine, and 0.52 mg/L Selenite. The B27 is "B-27TM Supplement (50X), minus vitamin A" (such as GIBCO® #12587010, or other products with the same composition) providing an embryonic neuron culture medium supplement. The "B-27™ Supplement (50X), minus vitamin A" contains Biotin, DL Alpha Tocopherol Acetate, DL Alpha-Tocopherol, bovine serum albumin (BSA) (fatty acid free Fraction V), Catalase, Human Recombinant Insulin, Human Transferrin, Superoxide Dismutase, Corticosterone, D-Galactose, Ethanolamine HCl, Glutathione (reduced), L-Carnitine HCl, Linoleic Acid, Linolenic Acid, Progesterone, Putrescine 2HCl, Sodium Selenite, and T3 (triodo-I-thyronine). The solvent of the ITSX is an EBSS solution (Earle's balanced salt solution), and the solute and concentration are as follows: insulin 1 g/L; transferrin 0.55 g/L; sodium selenite 0.00067 g/L; ethanolamine 0.2 g/L. The GLUTAMAX™ is an advanced cell culture additive that can directly replace L-glutamine in a cell culture medium. The GLUTAMAX™ is "GLUTAMAX™ Supplement" (such as GIBCO® #35050061, or other products with the same composition). The Y-27632 is "Y-27632 dihydrochloride (an ATP-competitive ROCK-I and ROCK-II inhibitor, Ki is 220 nM and 300 nM, respectively)" (such as MCE #129830-38-2, or other products with the same composition).

In a specific embodiment of the present invention, the brand number of the ternary antibacterial and antifungal agent (penicillin-streptomycin-amphotericin B) is GIBCO® #15240062; the brand number of the HEPES is GIBCO® #15630080; the brand number of the GLUTAMAX™ is GIBCO® #35050061: the brand number of the human recombinant protein EGF is PEPROTECH® AF-100-15-100; the brand number of the human recombinant protein bFGF is PEPROTECH® AF-100-18B-50; the brand number of the recombinant protein HGF is PEPROTECH® AF-100-39-100; the brand number of the human recombinant protein Wnt-3a is R&D 5036-WN-500; the brand number of the human recombinant protein Noggin is Shanghai Novoprotein #C018; the brand number of the SB202190 is SIGMA® #S7067; the brand number of the A83-01 is Tocris #2939; the brand number of the PRIMOCIN™ is Invivogene #ant-pm-1; the brand number of the N-acetyl-L-cysteine is SIGMA® #A9165; the brand number of the Nicotinamide is SIGMA® #N0636; the brand number of the N-2 Supplement is GIBCO® 17502001; the brand number of the cortisol is SIGMA® #H0888; the brand number of the B27 is GIBCO® #12587010; the brand number of the ITS-X is GIBCO® #51500056; the brand number of the Y-27632 is MCE #129830-38-2; and the brand number of the Advanced DMEM/F12 medium is GIBCO® #12634010, which is a cell culture medium comprising ethanolamine, glutathione, ascorbic acid, insulin, transferrin, bovine serum albumin, and trace elements, including sodium selenite, ammonium metavanadate, copper sulfate, and manganese chloride.

Further, the medium for culturing colorectal cancer primary cells can exist in two forms:

First, the medium for culturing colorectal cancer primary cells is a solution formed by mixing the ternary antibacterial and antifungal agent, the HEPES, the GLUTAMAX™, the human recombinant protein EGF, the human recombinant protein bFGF, the human recombinant protein HGF, the human recombinant protein Wnt-3a, the human recombinant protein Noggin, the SB202190, the A83-01, the PRIMOCIN™, the N-acetyl-L-cysteine, the Nicotinamide, the N-2 Supplement, the cortisol, the B27, the ITS-X, the Y-27632, and the Advanced DMEM/F12 medium.

After preparation, the medium needs to be filtered and sterilized with a 0.22 μM syringe filter (Millipore SLGP033RS) and can be preserved at 4° C. for two weeks.

Second, each component in the medium for culturing colorectal cancer primary cells exists alone, and the medium is prepared according to a formula when used.

Much further, the human recombinant protein EGF, the human recombinant protein bFGF, the human recombinant protein HGF, the human recombinant protein Wnt-3a, and the human recombinant protein Noggin can exist in the form of stock solutions (mother solutions) (long-stem preservation at −80° C.), which can specifically be 1.000 times stock solutions (mother solutions). The SB202190, the N-acetyl-L-cysteine, the Nicotinamide, the cortisol and the Y-27632 can exist in the form of stock solutions (mother solutions) (long-stem preservation at −20° C.). which can specifically be 1.000 times stock solutions (mother solutions). The A83-01 can exist in the form of a stock solution (mother solution) (long-term preservation at −20° C.), which can specifically be a 100.000 times stock solution (mother solution).

The 1.000× human recombinant protein EGF stock solution is composed of a human recombinant protein EGF, a BSA and a PBS, wherein a final concentration of the human recombinant protein EGF is 20 μg/mL, a final concentration of the BSA is 0.01 g/mL, and the balance is the PBS.

The 1.000× human recombinant protein bFGF stock solution is composed of a human recombinant protein bFGF, a BSA and a PBS, wherein a final concentration of the human recombinant protein bFGF is 20 μg/mL, a final concentration of the BSA is 0.01 g/mL, and the balance is the PBS.

The 1.000× human recombinant protein HGF stock solution is composed of a human recombinant protein HGF, a BSA and a PBS, wherein a final concentration of the human recombinant protein HGF is 20 μg/mL, a final concentration of the BSA is 0.01 g/mL, and the balance is the PBS.

The 1.000× human recombinant protein Wnt-3a stock solution is composed of a human recombinant protein Wnt-3a, a BSA and a PBS, wherein a final concentration of the human recombinant protein Wnt-3a is 200 μg/mL, a final concentration of the BSA is 0.01 g/mL, and the balance is the PBS.

The 1,000× human recombinant protein Noggin stock solution is composed of a human recombinant protein Noggin, a BSA and a PBS, wherein a final concentration of the human recombinant protein Noggin is 100 μg/mL, a final concentration of the BSA is 0.01 g/mL, and the balance is the PBS.

Among the above five 1,000 times stock solutions, the BSA can exist in the form of a 100 times stock solution (mother solution) (prepared for current use), which is specifically composed of a BSA and a PBS, wherein a final concentration of the BSA (SIGMA® #A1933) is 0.1 g/mL, and the balance is the PBS.

In addition, the 1,000× SB202190 stock solution is composed of an SB202190 and a DMSO, wherein a final concentration of the SB202190 is 10 mM, and the balance is the DMSO.

The 100,000× A83-01 stock solution is composed of an A83-01 and a DMSO, wherein a concentration of the A83-01 is 25 mM, and the balance is the DMSO.

The 1,000× N-acetyl-L-cysteine stock solution is composed of N-acetyl-L-cysteine and ultra-pure water, wherein a concentration of the N-acetyl-L-cysteine is 0.5 M, and the balance is the ultra-pure water.

The 1,000× Nicotinamide stock solution is composed of Nicotinamide and ultra-pure water, wherein a concentration of the Nicotinamide is 5 M, and the balance is the ultra-pure water.

The 1,000× cortisol stock solution is composed of cortisol, absolute ethanol and ultra-pure water, wherein a final concentration of the cortisol is 25 μg/mL, a final concentration of the absolute ethanol is 5% (volume percentage), and the balance is the ultra-pure water.

The 1,000× Y-27632 is composed of Y-27632 and ultra-pure water, wherein a final concentration of the Y-27632 is 10 mM, and the balance is the ultra-pure water.

In the second aspect, the present invention claims a set of reagents for culturing colorectal cancer primary cells.

The set of reagents claimed in the present invention can be any of the following:

(A1) all or part of the medium described in the first aspect above: a sample dissociation solution, a sample preservation solution and a sample washing solution.

(A2) the medium described in the first aspect above and a cell isolation buffer.

(A3) the (A1) and all or part of the following reagents: a cell dissociation solution, a dissociation stop solution and a cell cryopreservation solution.

(A4) the (A2) and all or part of the following reagents: a cell dissociation solution, a dissociation stop solution and a cell cryopreservation solution.

The sample dissociation solution is composed of a collagenase I, a collagenase II, a collagenase IV and a PBS: wherein, a final concentration of the collagenase I in the sample dissociation solution is 150-250 U/mL (such as 200 U/mL): a final concentration of the collagenase II in the sample dissociation solution is 150-250 U/mL (such as 200 U/mL): a final concentration of the collagenase IV in the sample dissociation solution is 50-150 U/mL (such as 100 U/mL); and the balance is the PBS.

The unit U of a collagenase (the collagenase I, the collagenase II, or the collagenase IV) is defined by the enzyme activity of a protease: the collagenase (the collagenase I, the collagenase II, or the collagenase IV) is treated with 1 U of the protease for 5 hours at 37° C. and pH 7.5, and 1 μmol of L-leucine can be released.

In a specific embodiment of the present invention, the brand number of the collagenase I is GIBCO® #17100-017; the brand number of the collagenase II is GIBCO® #17101-015: the brand number of the collagenase IV is GIBCO® #17104-019; and the brand number of the PBS is GIBCO® #21-040-CVR.

The sample preservation solution is composed of a fetal bovine serum, a ternary antibacterial and antifungal agent (penicillin-streptomycin-amphotericin B), an HEPES and an HBSS (Hank's balanced salt solution): wherein, a final concentration of the fetal bovine serum in the sample preservation solution is 1-5% (such as 2%. % represents a volume percentage): a final concentration of penicillin in the ternary antibacterial and antifungal agent (penicillin-streptomycin-amphotericin B) in the sample preservation solution is 100-200 U/mL (such as 100 U/mL): a final concentration of streptomycin in the ternary antibacterial and antifungal agent (penicillin-streptomycin-amphotericin B) in the sample preservation solution is 100-200 μg/mL (such as 100 μg/mL): a final concentration of amphotericin B in the ternary antibacterial and antifungal agent (penicillin-streptomycin-amphotericin B) in the sample preservation solution is 250-500 ng/ml (such as 250 ng/mL); a final concentration of the HEPES in the sample preservation solution is 8-12 mM (such as 10 mM); and the balance is the HBSS.

Further, the composition of the ternary antibacterial and antifungal agent (penicillin-streptomycin-amphotericin B) is as follows: each milliliter contains 10.000 units of penicillin (base). 10,000 μg of streptomycin (base) and 25 μg of amphotericin B. The ternary antibacterial and antifungal agent (penicillin-streptomycin-amphotericin B) is "Antibiotic-Antimycotic. 100X" (such as GIBCO® #15240062, or other products with the same composition). Each milliliter of the "Antibiotic-Antimycotic. 100X" contains 10.000 units of penicillin (base). 10.000 μg of streptomycin (base) and 25 μg of amphotericin B. and penicillin G (sodium salt), streptomycin sulfate and amphotericin B in the form of 0.85% salt solutions are used as Fungizone R antifungal agents.

In a specific embodiment of the present invention, the brand number of the fetal bovine serum is GIBCO® #16000-044; the brand number of the ternary antibacterial and antifungal agent (penicillin- streptomycin-amphotericin B)

is GIBCO® #15240062; the brand number of the HEPES is GIBCO® #15630080; and the brand number of the HBSS is GIBCO® #14170161.

The sample washing solution is composed of a ternary antibacterial and antifungal agent (penicillin-streptomycin-amphotericin B) and a PBS: wherein. a final concentration of penicillin in the ternary antibacterial and antifungal agent (penicillin-streptomycin-amphotericin B) in the sample washing solution is 100-200 U/mL (such as 100 U/mL); a final concentration of streptomycin in the ternary antibacterial and antifungal agent (penicillin-streptomycin-amphotericin B) in the sample washing solution is 100-200 μg/mL (such as 100 μg/mL): a final concentration of amphotericin B in the ternary antibacterial and antifungal agent (penicillin-streptomycin-amphotericin B) in the sample washing solution is 250-500 ng/mL (such as 250 ng/mL); and the balance is the PBS.

Further, the composition of the ternary antibacterial and antifungal agent (penicillin-streptomycin-amphotericin B) is as follows: each milliliter contains 10.000 units of penicillin (base). 10.000 μg of streptomycin (base) and 25 μg of amphotericin B. The ternary antibacterial and antifungal agent (penicillin-streptomycin-amphotericin B) is "Antibiotic-Antimycotic. 100X" (such as GIBCO® #15240062, or other products with the same composition). Each milliliter of the "Antibiotic-Antimycotic. 100X" contains 10.000 units of penicillin (base), 10,000 μg of streptomycin (base) and 25 μg of amphotericin B. and penicillin G (sodium salt), streptomycin sulfate and amphotericin B in the form of 0.85% salt solutions are used as Fungizone R antifungal agents.

In a specific embodiment of the present invention, the brand number of the ternary antibacterial and antifungal agent (penicillin-streptomycin-amphotericin B) is GIBCO® #15240062; and the brand number of the PBS is GIBCO® #21-040-CVR.

The cell isolation buffer is composed of a ternary antibacterial and antifungal agent (penicillin-streptomycin-amphotericin B), heparin sodium and a PBS: wherein, a final concentration of penicillin in the ternary antibacterial and antifungal agent (penicillin-streptomycin-amphotericin B) is 100-200 U/mL (such as 100 U/mL): a final concentration of streptomycin in the ternary antibacterial and antifungal agent (penicillin-streptomycin-amphotericin B) is 100-200 μg/mL (such as 100 μg/mL): a final concentration of amphotericin B in the ternary antibacterial and antifungal agent (penicillin-streptomycin-amphotericin B) is 250-500 ng/ml (such as 250 ng/ml): a final concentration of the heparin sodium is 10 IU/mL; and the balance is the PBS.

Further, the composition of the ternary antibacterial and antifungal agent (penicillin-streptomycin-amphotericin B) is as follows: each milliliter contains 10,000 units of penicillin (base). 10.000 μg of streptomycin (base) and 25 μg of amphotericin B. The ternary antibacterial and antifungal agent (penicillin-streptomycin-amphotericin B) is "Antibiotic-Antimycotic. 100X" (such as GIBCO® #15240062, or other products with the same composition). Each milliliter of the "Antibiotic-Antimycotic. 100X" contains 10.000 units of penicillin (base). 10.000 μg of streptomycin (base) and 25 μg of amphotericin B. and penicillin G (sodium salt). streptomycin sulfate and amphotericin B in the form of 0.85% salt solutions are used as Fungizone® antifungal agents.

In a specific embodiment of the present invention, the brand number of the ternary antibacterial and antifungal agent (penicillin-streptomycin-amphotericin B) is GIBCO® #15240062; the brand number of the heparin sodium is SOLARBIOR #H8270); and the brand number of the PBS is GIBCO #21-040-CVR.

The composition of the cell dissociation solution is as follows: every 10 mL of the cell dissociation solution contains 4-6 mL (such as 5 mL) of a cell dissociation reagent comprising collagenolytic and proteolytic enzymes in D-PBS and 0.5 mM EDTA (ACCUTASE), EDTA with a final concentration of 5 mM (that is, 10 μL of 0.5 M EDTA), 1.5-2.5 mL (such as 2 mL) of an enzyme solution comprising a recombinant protease having Lys-C and Arg-C protease activity and 200 mg/L KCl, 200 mg/L KH$_2$PO4, 8,000 mg/L NaCl, 2,160 mg/L Na2HPO4-7H2O, 457.6 mg/L EDTA (TRYPLE Express), and the balance of PBS.

Further, the ACCUTASE is "STEMPRO™ ACCUTASE™ Cell Dissociation Reagent" (such as GIBCO® #A11105-01, or other products with the same composition). The Accutase is a single-component enzyme and is dissolved in a solution of D-PBS and 0.5 mM EDTA. The TRYPLE Express is "TRYPLE™ Express Enzyme (1X), no phenol red" (such as GIBCO® #12604013, or other products with the same composition). The "TRYPLE™ Express Enzyme (1X), no phenol red" contains 200 mg/L KCl. 200 mg/L KH$_2$PO$_4$. 8.000 mg/L NaCl. 2.160 mg/L Na$_2$HPO$_4$·7H$_2$O. 457.6 mg/L EDTA, and a recombinant protease.

In a specific embodiment of the present invention, the brand number of the ACCUTASE is GIBCO® #A11105-01: the brand number of the 0.5 M EDTA is INVITROGEN® #AM9261; the brand number of the TRYPLE Express is Gibco #12604013; and the brand number of the PBS is TRYPLE #21-040-CVR.

The dissociation stop solution is composed of a fetal bovine serum, a ternary antibacterial and antifungal agent (penicillin-streptomycin-amphotericin B) and a Dulbecco's modified eagle medium (DMEM): wherein, a final concentration of the fetal bovine serum in the dissociation stop solution is 8-12% (such as 10%. % represents a volume percentage): a final concentration of penicillin in the ternary antibacterial and antifungal agent (penicillin-streptomycin-amphotericin B) in the dissociation stop solution is 100-200 U/mL (such as 100 U/mL); a final concentration of streptomycin in the ternary antibacterial and antifungal agent (penicillin-streptomycin-amphotericin B) in the dissociation stop solution is 100-200 μg/mL (such as 100 μg/mL): a final concentration of amphotericin B in the ternary antibacterial and antifungal agent (penicillin-streptomycin-amphotericin B) in the dissociation stop solution is 250-500 ng/mL (such as 250 ng/mL); and the balance is the DMEM.

Further, the composition of the ternary antibacterial and antifungal agent (penicillin-streptomycin-amphotericin B) is as follows: each milliliter contains 10,000 units of penicillin (base). 10.000 μg of streptomycin (base) and 25 μg of amphotericin B. The ternary antibacterial and antifungal agent (penicillin-streptomycin-amphotericin B) is "Antibiotic-Antimycotic. 100X" (such as GIBCO® #15240062, or other products with the same composition). Each milliliter of the "Antibiotic-Antimycotic. 100X" contains 10.000 units of penicillin (base). 10.000 μg of streptomycin (base) and 25 μg of amphotericin B. and penicillin G (sodium salt), streptomycin sulfate and amphotericin B in the form of 0.85% salt solutions are used as FUNGIZONE® antifungal agents.

In a specific embodiment of the present invention, the brand number of the fetal bovine serum is GIBCO® #16000-044; the brand number of the ternary antibacterial and antifungal agent (penicillin- streptomycin-amphotericin B)

is GIBCO® #15240062; and the brand number of the DMEM is GIBCO® #11965-092.

The cell cryopreservation solution is composed of an Advanced DMEM/F12 medium, a DMSO and a 1% methyl cellulose solution: wherein, a volume ratio of the Advanced DMEM/F12 medium, the DMSO and the 1% methyl cellulose solution is 20:2: (0.8-1.2), such as 20:2:1; and the 1% methyl cellulose solution is a methyl cellulose aqueous solution with a concentration of 1 g/100 ml.

In a specific embodiment of the present invention, the brand number of the Advanced DMEM/F12 medium is GIBCO® #12634010; the brand number of the DMSO is SIGMA® #D2438; and the brand number of the methyl cellulose is SIGMA® #M7027.

The sample preservation solution can be used for temporary preservation of a sample in vitro and can maintain the activity of cells in the sample within a short time after the sample has been in vitro. The sample preservation solution can be preserved for 1 month at 4° C. after preparation.

The sample washing solution can be used for washing and disinfection of the sample. The sample washing solution needs to be prepared for current use.

The sample dissociation solution can be used for dissociation of the sample and can dissociate colorectal cancer solid tumor primary cells in the sample from the tissues. The sample dissociation solution needs to be prepared for current use, and the collagenase I, the collagenase II and the collagenase IV therein can be preserved at −20° C. for a long term in the form of stock solutions (mother solutions), which can specifically be 10 or 20 times stock solutions (mother solutions). The 10× collagenase I stock solution is composed of the collagenase I and a PBS: a final concentration of the collagenase I is 2.000 U/mL: the 10× collagenase II stock solution is composed of the collagenase II and a PBS: a final concentration of the collagenase II is 2.000 U/mL: the balance is the PBS: the 20× collagenase IV stock solution is composed of the collagenase IV and a PBS: a final concentration of the collagenase IV is 2.000 U/mL; and the balance is the PBS. The enzyme activities of the collagenase I, the collagenase II and the collagenase IV are defined above.

The cell isolation buffer is used for suspending cells in the ascites to prepare for density gradient isolation of the cells. The cell isolation buffer can be preserved at 4° C. for 1 month after preparation.

The cell dissociation solution can be used for dissociation and passage of cell masses, and can dissociate colorectal cancer tumor masses into single cells. The cell dissociation solution needs to be prepared for current use.

The dissociation stop solution can be used for stopping the process of sample dissociation or cell dissociation. The dissociation stop solution can be preserved at 4° C. for one month after preparation.

The cell cryopreservation solution needs to be prepared for current use. The 1% methyl cellulose solution can be preserved for a long term at 4° C.

In the third aspect, the present invention claims any of the following applications:
(B1) an application of the medium described in the first aspect above in culture of colorectal cancer primary cells:
(B2) an application of the set of reagents described in (A1) or (A3) in the second aspect above in culture of colorectal cancer solid tumor primary cells; and
(B3) an application of the set of reagents described in (A2) or (A4) in the second aspect above in culture of colorectal cancer ascites primary tumor cells.

In the fourth aspect, the present invention claims a method for culturing colorectal cancer primary cells. The method for culturing colorectal cancer primary cells according to the present invention is method A or method B:

Method A: a method for culturing colorectal cancer solid tumor primary cells may include the following steps:
(a1) dissociating colorectal cancer solid tumor tissues with the sample dissociation solution described in the second aspect above to obtain colorectal cancer solid tumor primary cells; and
(a2) performing suspension culture with the medium described in the first aspect above on the colorectal cancer solid tumor primary cells dissociated in (a1).

Method B: a method for culturing colorectal cancer ascites primary tumor cells may include the following steps:
(b1) isolating colorectal cancer ascites primary tumor cells from colorectal cancer ascites; and
(b2) performing suspension culture with the medium described in the first aspect above on the colorectal cancer ascites primary tumor cells isolated in (b1).

Further, in (a1), the colorectal cancer solid tumor tissues can be dissociated with the sample dissociation solution according to a method including the following steps: treating the cut colorectal cancer solid tumor tissues (for example, cut into 0.8-1.2 $mm^3$ pieces) with the sample dissociation solution preheated at 37° C. according to an amount of 0.1-0.3 mL (such as 0.1 mL) of the sample dissociation solution per mg of tissues, and dissociating the sample at 37° C. for 15 minutes to 3 hours. The dissociation of the sample is observed under a microscope every 15 minutes until a large number of single cells are observed.

Further, in (b1), the colorectal cancer ascites primary tumor cells can be isolated from the colorectal cancer ascites according to a method including the following steps: suspending cells in the colorectal cancer ascites with the cell isolation buffer described in the second aspect above, and then obtaining the colorectal cancer ascites primary tumor cells by means of density gradient centrifugation (using a Ficoll lymphocyte isolation solution).

Further, in (a2), suspension culture can be performed with the colorectal cancer solid tumor primary cell medium on the colorectal cancer solid tumor primary cells according to a method including the following steps:
performing suspension culture in a cell culture vessel M with the medium on the colorectal cancer solid tumor primary cells at 37° C. and 5% $CO_2$, and changing the medium every 2-4 days (such as 3 days), until the cells form masses with a diameter of 50-80 μm (such as 80 μm).

Further, in (b2), suspension culture can be performed with the medium on the colorectal cancer ascites primary tumor cells according to a method including the following steps: performing suspension culture in a cell culture vessel M with the medium on the colorectal cancer ascites primary tumor cells at 37° C. and 5% $CO_2$, and changing the medium every 2-4 days (such as 3 days), until the cells form masses with a diameter of 50-80 μm (such as 80 μm).

The initial seeding density may be $10^5$ cells/$cm^2$ bottom area of the vessel. Taking a six-pore plank as an example, the cells are planked with a density of $10^6$ cells per pore.

The cell culture vessel M may be any of the following: (I) a cell culture vessel made of polystyrene, a cell culture vessel made of polycarbonate, a cell culture vessel made of polymethyl methacrylate, a cell culture vessel made of COC resin, a cell culture vessel made of cyclic olefin polymer, or a cell culture vessel with a low-attachment-surface; and (II)

a cell culture vessel modified from the cell culture vessel in (I) by a perfluoro (1-butenyl vinyl ether) polymer (CY-TOP").

Further, the cell culture vessel is a cell culture dish, a cell culture pore plate, or a microplate chip for cell culture.

In (II), the cell culture vessel in (I) can be modified by the CYTOP® according to a method including the following steps: etching the cell culture vessel in (I) with pure oxygen under a power of 20 W for 3 minutes; and then covering the surface of the cell culture vessel with a 1% CYTOP® solution, and drying the 1% CYTOP® solution in the air to complete the CYTOP® modification.

The CYTOP solution is an "amorphous fluoropolymer solution" having the composition as follows: every 100 ml of the 1% CYTOP® solution contains 1 mL of the amorphous fluoropolymer CYTOP® CTL-809M_and the balance of fluorocarbon oil.

Further, before (a1), the following steps of treating the colorectal cancer solid tumor tissues before dissociation may be further included: washing the surface of a colorectal cancer solid tumor tissue sample with ethanol having a volume percentage of 70-75% (such as 75%) for 10 to 30 seconds: washing the colorectal cancer solid tumor tissue sample with the sample washing solution 10-20 times (such as 10 times), and washing the colorectal cancer solid tumor tissue sample with a sterile PBS solution 5-10 times (such as 5 times); and then removing components such as impurities, connective tissues, adipose tissues, and necrotic tissues that affect the culture of the primary cells from the colorectal cancer solid tumor tissue sample.

The steps of treating the colorectal cancer solid tumor tissues before dissociation need to be operated on ice, and the entire operation steps need to be completed within 10 minutes.

Further, the in vitro time for treating the colorectal cancer solid tumor tissue sample before dissociation is within 2 hours, and the sample is preserved in the sample preservation solution all the time prior to the treatment before dissociation.

Further, in (a1), after the colorectal cancer solid tumor tissues are dissociated with the sample dissociation solution, the following steps may be further included: stopping the dissociation reaction with the dissociation stop solution having a 8-15 times (such as 10 times) volume, and collecting a cell suspension: filtering the cell suspension with a 100 μm or 40 μm sterile cell strainer to remove tissue debris and adherent cells: centrifuging 800-1,000 g (such as 800 g) at room temperature for 10-15 minutes (such as 10 minutes), and discarding the supernatant: then re-suspending cells with 3-5 mL (such as 5 mL) of sterile PBS: centrifuging 800-1,000 g (such as 800 g) again at room temperature for 10-15 minutes (such as 10 minutes), and discarding the supernatant; and re-suspending the cell precipitate with the medium described in the first aspect above, observing a cell state under a microscope, and counting cells.

Further, before (b1), a step of treating a colorectal cancer ascites sample before isolation is further included: removing components such as impurities and clots that affect cell density gradient isolation from the colorectal cancer ascites sample.

Further, in (a2), the following step may be further included: when the colorectal cancer solid tumor primary cells form masses with a diameter of 50-80 μm (such as 80 μm), passaging the colorectal cancer solid tumor primary cells.

Further, in (b2), the following step may be further included: when the colorectal cancer ascites primary tumor cells form masses with a diameter of 50-80 μm (such as 80 μm), passaging the colorectal cancer ascites primary tumor cells.

A cell dissociation solution used during the passaging is the cell dissociation solution described in the second aspect above.

A dissociation stop solution used during the passaging is the dissociation stop solution described in the second aspect above.

Much further, the dissociation temperature used during the passaging is 37° C.

More specifically; the passaging step includes: collecting the cell masses to be passaged, washing the cell masses with a sterile PBS solution after centrifugation, centrifuging again, then re-suspending the cell masses with the cell dissociation solution, dissociating at 37° C. until the cell masses are all dissociated into single cells, stopping the dissociation reaction with the dissociation stop solution (the amount may be 5-10 times, such as 10 times the volume), and collecting a cell suspension: re-suspending the cell precipitate with the medium described in the first aspect above after centrifugation, counting cells, and performing suspension culture on the cells by means of the cell culture vessel M described above (the initial seeding density may be $10^5$ cells/cm² bottom area of the vessel, and taking a six-pore plank as an example, the cells are planked with a density of $10^6$ cells per porc) at 37° C. and 5% $CO_2$. All the centrifugation in the above passaging step may specifically be 800-1,000 g (such as 800 g) centrifugation at room temperature for 10-20 minutes (such as 10 minutes).

Further, the method may further include a step of cryopreserving and/or resuscitating the colorectal cancer solid tumor primary cells or the colorectal cancer ascites primary tumor cells after 2-3 passaging expansions. A cell cryopreservation solution used during the cryopreserving is the cell cryopreservation solution described in the second aspect above.

Much further, the specific steps of the cryopreserving include: collecting the cell masses to be cryopreserved, washing the cell masses with a sterile PBS solution after centrifugation, centrifuging again, then re-suspending the cell masses with the cell dissociation solution, dissociating at 37° C. until the cell masses are all dissociated into single cells, stopping the dissociation reaction with the dissociation stop solution (the amount may be 5-10 times, such as 10 times the volume), and collecting a cell suspension: re-suspending the cell precipitate according to a density of $0.5-2 \times 10^6$/mL (such as $10^6$/mL) by using the cell cryopreservation solution after centrifugation, cryopreserving with a gradient cooling box overnight, and then transferring the cells to liquid nitrogen for long-term preservation. All the centrifugation in the above cryopreserving step may specifically be 800-1,000 g (such as 800 g) centrifugation at room temperature for 10-20 minutes (such as 10 minutes).

Much further, the specific steps of the resuscitating include: taking out cryopreservation tubes containing cells to be resuscitated from the liquid nitrogen, and quickly thawing the cells in sterile water at 37-39° C. (such as 37° C.): re-suspending the cell precipitate with the medium described in the first aspect above after centrifugation (for example, 800-1,000 g, such as 800 g centrifugation at room temperature for 5-10 minutes, such as 10 minutes), then performing suspension culture on the cells with the cell culture vessel M described above (the initial seeding density may be $10^5$ cells/cm² bottom area of the vessel), and resuscitating each tube of cells ($10^6$ cells) to a 3.5 cm culture dish, wherein the culture conditions are 37° C. and 5% $CO_2$.

In the fifth aspect, the present invention claims any of the following reagents:

(C1) a colorectal cancer solid tumor tissue sample dissociation solution, which is the sample dissociation solution described in the second aspect above:

(C2) a colorectal cancer solid tumor tissue sample preservation solution, which is the sample preservation solution described in the second aspect above; and (C3) a colorectal cancer ascites cell isolation buffer, which is the cell isolation buffer described in the second aspect above.

In the sixth aspect, the present invention claims any of the following applications:

(D1) an application of the sample dissociation solution described in (C1) of the fifth aspect above in dissociation of colorectal cancer solid tumor primary cells from colorectal cancer solid tumor tissues.

(D2) an application of the sample preservation solution described in (C2) of the fifth aspect above in preservation of colorectal cancer solid tumor tissues.

(D3) an application of the cell isolation buffer described in (C3) of the fifth aspect above in isolation of colorectal cancer ascites primary tumor cells from colorectal cancer ascites.

In the seventh aspect, the present invention claims any of the following methods:

(E1) a method for dissociating colorectal cancer solid tumor primary cells from colorectal cancer solid tumor tissues, including (a1) of the method described in the fourth aspect above.

(E2) a method for preserving colorectal cancer solid tumor tissues, including the following step: placing the newly isolated colorectal cancer solid tumor tissues in the sample preservation solution described in the second aspect above for preserving within 2 hours.

(E3) a method for isolating colorectal cancer ascites primary tumor cells from colorectal cancer ascites, including (b1) in the fourth aspect above.

In the above aspects, the colorectal cancer may be primary colorectal cancer. The pathological type is colorectal cancer or colorectal cancer metastasis lesion. The pathological stage is stage II or stage III or stage IV.

Further, the sample used when the colorectal cancer primary cells are isolated from the colorectal cancer solid tumor tissues may be a stage II or III or IV colorectal cancer sample. The sample used when the colorectal cancer primary cells are isolated from the colorectal cancer ascites is a stage IV colorectal cancer sample.

In the above aspects, the colorectal cancer primary cells may be colorectal cancer solid tumor primary cells or colorectal cancer ascites primary tumor cells.

In the above aspects, the colorectal cancer primary cells may be isolated from surgical samples (solid tumor samples), colonoscopy puncture samples or ascites samples of colorectal cancer patients. The colorectal cancer solid tumor tissue sample obtained from the surgical sample is preferably more than 20 mg. The ascites sample is preferably not less than 50 mL. The number of the colonoscopy puncture samples (solid tumor samples) is not less than 2.

In the present invention, all the above-mentioned PBS may be 1×PBS, with a pH value of 7.3-7.5. A specific composition of the PBS is as follows: the solvent is water, and the solutes and concentrations are: $KH_2PO_4$ 144 mg/L, NaCl 9,000 mg/L, and Na: $HPO_4 \cdot 7H_2O$ 795 mg/L.

DETAILED DESCRIPTION OF THE INVENTION

Figure 1:
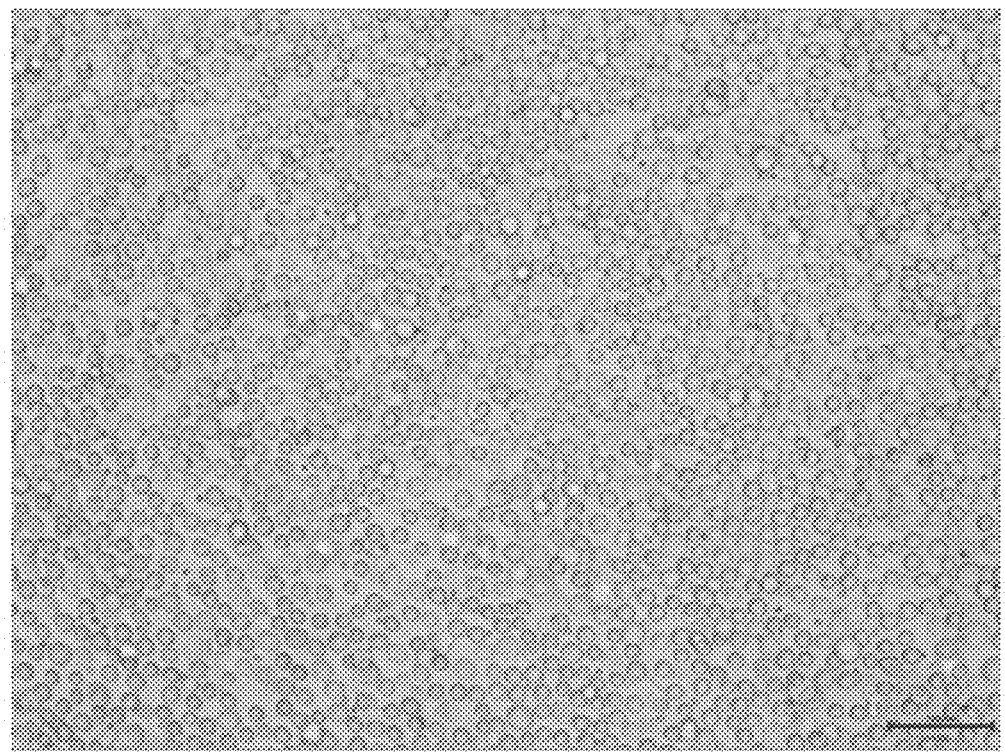
FIG. 1 shows single cells obtained after treatment of colorectal cancer tissues. The scale is 100 µm, 100 times magnification.

The following embodiments facilitate better understanding of the present invention, but do not limit the present invention. The experimental methods in the following embodiments are conventional methods, unless otherwise specified. The test materials used in the following embodiments are purchased from conventional biochemical reagent stores, unless otherwise specified.

Embodiment 1. Preparation of Reagents for Culturing Colorectal Cancer Solid Tumor Primary Cells 1. Sample Preservation Solution (100 mL)

A specific formula of the sample preservation solution (100 mL) was shown in Table 1.

TABLE 1

Sample preservation solution (100 mL)

| Reagent | Brand number | Amount | Final concentration |
|---|---|---|---|
| Fetal bovine serum | GIBCO ® #16000-044 | 2 mL | 2% |
| Ternary antibacterial and antifungal agent | GIBCO ® #15240062 | 1 mL | 1% |
| HEPES | GIBCO ® #15630080 | 1 mL | 10 mM |
| HBSS | GIBCO ® #14170161 | Made up to 100 mL | |

After preparation, the sample preservation solution was dispensed in 15 mL centrifuge tubes, 5 mL per tube. The sample preservation solution can be preserved at 4° C. for 1 month after being dispensed.

2. Sample Washing Solution (100 mL)

A specific formula of the sample washing solution (100 mL) was shown in Table 2.

TABLE 2

Sample washing solution (100 mL)

| Reagent | Brand number | Amount | Final concentration |
|---|---|---|---|
| Ternary antibacterial and antifungal agent | GIBCO ® #15240062 | 1 mL | 1% |
| PBS | GIBCO ® #21-040-CVR | Made up to 100 mL | |

The sample washing solution was prepared for current use.

3. Sample Dissociation Solution (10 mL)

A specific formula of the sample dissociation solution (10 mL) was shown in Table 3.

TABLE 3

Sample dissociation solution (10 mL)

| Reagent | Brand number | Amount | Final concentration |
|---|---|---|---|
| 10× collagenase I | 10× stock solution | 1 mL | 200 U/mL |
| 10× collagenase II | 10× stock solution | 1 mL | 200 U/mL |
| 20× collagenase IV | 20× stock solution | 0.5 mL | 100 U/mL |
| PBS | GIBCO ® #21-040-CVR | Made up to 10 mL | |

Note: the sample dissociation solution was prepared for current use.

In Table 3, the preparations of the collagenase stock solutions were shown in Tables 4-6.

TABLE 4

10× collagenase I stock solution (100 mL)

| Reagent | Brand number | Amount | Final concentration |
|---|---|---|---|
| Collagenase I | GIBCO ® #17100-017 | 1 g | 2,000 U/mL |
| PBS | GIBCO ® #21-040-CVR | Made up to 100 mL | |

After preparation, the 10× collagenase I stock solution was dispensed in 1.5 mL sterile centrifuge tubes, 1 mL per tube. The stock solution can be preserved for a long term at −20° C.

TABLE 5

10× collagenase II stock solution (100 mL)

| Reagent | Brand number | Amount | Final concentration |
|---|---|---|---|
| Collagenase II | GIBCO ® #17101-015 | 1 g | 2,000 U/mL |
| PBS | GIBCO ® #21-040-CVR | Made up to 100 mL | |

After preparation, the 10× collagenase II stock solution was dispensed in 1.5 mL sterile centrifuge tubes, 1 mL per tube. The stock solution can be preserved for a long term at −20° C.

TABLE 6

20× collagenase IV stock solution (100 mL)

| Reagent | Brand number | Amount | Final concentration |
|---|---|---|---|
| Collagenase IV | GIBCO ® #17104-019 | 1 g | 2,000 U/mL |
| PBS | GIBCO ® #21-040-CVR | Made up to 100 mL | |

After preparation, the 20× collagenase IV stock solution was dispensed in 1.5 mL sterile centrifuge tubes, 1 mL per tube. The stock solution can be preserved for a long term at −20° C.

In Tables 4, 5 and 6, the unit U of the collagenase (the collagenase I or the collagenase IV) was defined by the enzyme activity of a protease: the collagenase (the collagenase I or the collagenase IV) was treated with 1 U of the protease for 5 hours at 37° C. and pH 7.5, and 1 μmol of L-leucine can be released.

4. Cell Dissociation Solution (10 mL)

A specific formula of the cell dissociation solution (10 mL) was shown in Table 7.

TABLE 7

Cell dissociation solution (10 mL)

| Reagent | Brand number | Amount | Final concentration |
|---|---|---|---|
| Accutase | GIBCO ® #A11105-01 | 5 mL | |
| 0.5M EDTA | Invitrogen#AM9261 | 10 μL | 5 mM |
| TrypLE Express | GIBCO ® #12604013 | 2 mL | |
| PBS | GIBCO ® #21-040-CVR | Made up to 10 mL | |

The cell dissociation solution was prepared for current use.

5. Dissociation Stop Solution (100 mL)

A specific formula of the dissociation stop solution (100 mL) was shown in Table 8.

TABLE 8

Dissociation stop solution (100 mL)

| Reagent | Brand number | Amount | Final concentration |
|---|---|---|---|
| Fetal bovine serum | GIBCO ® #16000-044 | 10 mL | 10% |
| Ternary antibacterial and antifungal agent | GIBCO ® #15240062 | 1 mL | 1% |

TABLE 8-continued

| Dissociation stop solution (100 mL) | | | |
|---|---|---|---|
| Reagent | Brand number | Amount | Final concentration |
| DMEM | GIBCO ® #11965-092 | Made up to 100 mL | |

The dissociation stop solution can be preserved at 4° C. for one month after preparation.

6. Colorectal Cancer Solid Tumor Primary Cell Medium (100 mL)

A specific formula of the colorectal cancer solid tumor primary cell medium (100 mL) was shown in Table 9.

TABLE 9

| Colorectal cancer solid tumor primary cell medium (100 mL) | | | |
|---|---|---|---|
| Reagent | Brand number | Amount | Final concentration |
| Ternary antibacterial and antifungal agent | GIBCO ® #15240062 | 1 mL | 1% |
| HEPES | GIBCO ® #15630080 | 1 mL | 10 mM |
| GLUTAMAX ™ | GIBCO ® #35050061 | 1 mL | 1% |
| 1,000× human recombinant protein EGF | 1,000× stock solution | 50-500 μL | 10-100 ng/mL |
| 1,000× human recombinant protein bFGF | 1,000× stock solution | 50-250 μL | 10-50 ng/mL |
| 1,000× human recombinant protein HGF | 1,000× stock solution | 25-125 μL | 5-25 ng/mL |
| 1,000× human recombinant protein Wnt-3a | 1,000× stock solution | 100-150 μL | 200-300 ng/mL |
| 1,000× human recombinant protein Noggin | 1,000× stock solution | 100-200 μL | 100-200 ng/mL |
| SB202190 | 1,000× stock solution | 50-100 μL | 5-10 μM |
| A83-01 | 100,000× stock solution | 1-5 μL | 0.25-1.25 μM |
| PRIMOCIN ™ | Invivogene#ant-pm-1 | 1 mL | 1% |
| N-acetyl-L-cysteine | 1,000× stock solution | 100-400 μL | 0.5-2 mM |
| Nicotinamide | 1,000× stock solution | 100-200 μL | 5-10 mM |
| N-2 Supplement | GIBCO ® #17502001 | 1 mL | 1% |
| 1,000× cortisol | 1,000× stock solution | 80-200 μL | 20-50 ng/mL |
| B27 | GIBCO ® #12587010 | 2 mL | 2% |
| ITS-X | GIBCO ® #51500056 | 1 mL | 1% |
| 1,000× Y-27632 | 1,000× stock solution | 50-200 μL | 5-20 μM |
| Advanced DMEM/F12 medium | GIBCO ® #12634010 | Made up to 100 ml | |

After preparation, the colorectal cancer solid tumor primary cell modium was filtered and sterilized with a 0.22 μM syringe filter (Millipore SLGP033RS), and can be preserved at 4° C. for two weeks.

In Table 9, the preparations of the human recombinant protein stock solutions were shown in Tables 11-15, the preparation of the SB202190 stock solution was shown in Table 16, the preparation of the A83-01 stock solution was shown in Table 17, the preparation of the N-acetyl-L-cysteine stock solution was shown in Table 18, the preparation of the Nicotinamide stock solution was shown in Table 19, the preparation of the cortisol stock solution was shown in Table 20, and the preparation of the Y-27632 stock solution was shown in Table 21. The preparation of a 100× BSA solution required when these stock solutions were prepared was shown in Table 10.

TABLE 10

| 100× BSA solution (1 mL) | | | |
|---|---|---|---|
| Reagent | Brand number | Amount | Final concentration |
| BSA | SIGMA ®#A1933 | 0.1 g | 0.1 g/mL |
| PBS | GIBCO ® #21-040-CVR | Made up to 1 mL | |

The 100× BSA solution was prepared for current use.

TABLE 11

| 1,000× human recombinant protein EGF stock solution (5 mL) | | | |
|---|---|---|---|
| Reagent | Brand number | Amount | Final concentration |
| Human recombinant protein EGF | PEPROTECH ® AF-100-15-100 | 100 μg | 20 μg/mL |
| 100× BSA solution | | 500 μL | 0.01 g/mL |
| PBS | GIBCO ® #21-040-CVR | Made up to 5 mL | |

After preparation, the 1,000× human recombinant protein EGF stock solution was dispensed in 1.5 mL sterile centrifuge tubes, and the stock solution can be preserved for a long term at −80° C.

TABLE 12

1,000× human recombinant protein bFGF stock solution (2.5 mL)

| Reagent | Brand number | Amount | Final concentration |
|---|---|---|---|
| Human recombinant protein bEGF | PEPROTECH ® AF-100-18B-50 | 50 μg | 20 μg/mL |
| 100× BSA solution | | 250 μL | 0.01 g/mL |
| PBS | GIBCO ® #21-040-CVR | Made up to 2.5 mL | |

After preparation, the 1,000× human recombinant protein bEGF stock solution was dispensed in 1.5 mL sterile centrifuge tubes, and the stock solution can be preserved for a long term at −80° C.

TABLE 13

1,000× human recombinant protein HGF stock solution (5 mL)

| Reagent | Brand number | Amount | Final concentration |
|---|---|---|---|
| Human recombinant protein HGF | PEPROTECH ® AF-100-39-100 | 100 μg | 20 μg/mL |
| 100× BSA solution | | 500 μL | 0.01 g/mL |
| PBS | GIBCO ® #21-040-CVR | Made up to 5 mL | |

After preparation, the 1,000× human recombinant protein HGF stock solution was dispensed in 1.5 mL sterile centrifuge tubes, and the stock solution can be preserved for a long term at −80° C.

TABLE 14

1,000× human recombinant protein Wnt-3a stock solution (2.5 mL)

| Reagent | Brand number | Amount | Final concentration |
|---|---|---|---|
| recombinant protein Wnt-3a | R&D ™ 5036-WN-500 | 500 μg | 200 μg/mL |
| 100× BSA solution | | 250 μL | 0.01 g/mL |
| PBS | GIBCO ® #21-040-CVR | Made up to 2.5 mL | |

After preparation, the 1,000× human recombinant protein Wnt-3a stock solution was dispensed in 1.5 mL sterile centrifuge tubes, and the stock solution can be preserved for a long term at −80° C.

TABLE 15

1,000× human recombinant protein Noggin stock solution (5 mL)

| Reagent | Brand number | Amount | Final concentration |
|---|---|---|---|
| Human recombinant protein Noggin | Shanghai NOVOPROTEIN ™ #C018 | 500 μg | 100 μg/mL |
| 100× BSA solution | | 500 μL | 0.01 g/mL |
| PBS | GIBCO ® #21-040-CVR | Made up to 5 mL | |

After preparation, the 1,000× human recombinant protein Noggin stock solution was dispensed in 1.5 mL sterile centrifuge tubes, and the stock solution can be preserved for a long term at −80° C.

TABLE 16

1,000× SB202190 stock solution (1.51 mL)

| Reagent | Brand number | Amount | Final concentration |
|---|---|---|---|
| SB202190 | SIGMA ® #S7067 | 5 mg | 10 mM |
| DMSO | | Made up to 1.51 mL | |

After preparation, the 1,000× SB202190 stock solution was dispensed in 0.5 mL sterile centrifuge tubes, and the stock solution can be preserved for a long term at −20° C.

TABLE 17

100,000× A83-01 stock solution (1.05 mL)

| Reagent | Brand number | Amount | Final concentration |
|---|---|---|---|
| A83-01 | TOCRIS ™ #2939 | 10 mg | 25 mM |
| DMSO | | Made up to 1.05 mL | |

After preparation, the 100,000× A83-01 stock solution was dispensed in 0.5 mL sterile centrifuge tubes, and the stock solution can be preserved for a long term at −20° C.

TABLE 18

1,000× N-acetyl-L-cysteine stock solution (5 mL)

| Reagent | Brand number | Amount | Final concentration |
|---|---|---|---|
| N-acetyl-L-cysteine | SIGMA ® #A9165 | 0.41 g | 0.5M |
| Ultra-pure water | | Made up to 5 mL | |

After preparation, the 1,000× N-acetyl-L-cysteine stock solution was dispensed in 0.5 mL sterile centrifuge tubes, and the stock solution can be preserved for a long term at −20° C.

TABLE 19

1,000× Nicotinamide stock solution (4 mL)

| Reagent | Brand number | Amount | Final concentration |
|---|---|---|---|
| Nicotinamide | SIGMA ® #N0636 | 2.44 g | 5M |
| Ultra-pure water | | Made up to 4 mL | |

After preparation, the 1,000× Nicotinamide stock solution was dispensed in 0.5 mL sterile centrifuge tubes, and the stock solution can be preserved for a long term at −20° C.

TABLE 20

1,000× cortisol stock solution (100 mL)

| Reagent | Brand number | Amount | Final concentration |
|---|---|---|---|
| Cortisol | SIGMA ® #H0888 | 2.5 mg | 25 μg/mL |
| Absolute ethanol | SIGMA ® #E7023 | 5 mL | 5% |
| Ultra-pure water | | Made up to 100 mL | |

After preparation, the 1,000× cortisol stock solution was dispensed in 1.5 mL sterile centrifuge tubes, and the stock solution can be preserved for a long term at −20° C.

TABLE 21

1,000× Y-27632 stock solution (3.125 mL)

| Reagent | Brand number | Amount | Final concentration |
|---|---|---|---|
| Y-27632 | MCE#129830-38-2 | 10 mg | 10 mM |
| Ultra-pure water | | Made up to 3.125 mL | |

After preparation, the 1,000× Y-27632 stock solution was dispensed in 0.5 mL sterile centrifuge tubes, and the stock solution can be preserved for a long term at −20° C.

7. Cell Cryopreservation Solution

A specific formula of the cell cryopreservation solution was shown in Table 22.

TABLE 22

Cell cryopreservation solution

| Reagent | Brand number | Amount |
|---|---|---|
| Advanced DMEM/F12 medium | GIBCO ® #12634010 | 20 mL |
| DMSO | SIGMA ® #D2438 | 2 mL |
| 1% methyl cellulose solution | | 1 mL |

The cell cryopreservation solution was prepared for current use.

In Table 22, the preparation of the 1% methyl cellulose solution was shown in Table 23.

TABLE 23

1% methyl cellulose solution (10 mL)

| Reagent | Brand number | Amount | Final concentration |
|---|---|---|---|
| Methyl cellulose | SIGMA ® #M7027 | 0.1 g | 10 g/L |
| Ultra-pure water | | Made up to 10 mL | |

The 1% methyl cellulose solution can be preserved for a long time at 4° C. after preparation.

Embodiment 2. Obtaining of Postoperative Samples of Colorectal Cancer Solid Tumors 1. Cooperation with a top three hospital, the cooperation had passed the formal medical ethics review.

2. Attending physicians selected participating patients according to the clinical indications specified in the medical guidelines, and selected appropriate samples according to the intraoperative clinical indications for in vitro culture. The selection criteria for samples were: primary colorectal cancer, pathological stage: stage II, stage III or stage IV, colorectal cancer or colorectal cancer metastasis lesions of various pathological types, and colorectal cancer surgical samples with a weight of more than 20 mg.

3. The attending physicians provided basic clinical information such as patient's gender, age, medical history, family history, smoking history, pathological stage type, and clinical diagnosis. Information related to patient's privacy, such as patient's name and ID number, was concealed and replaced with a uniform experiment number. The naming principle of the experiment number was the eight-digit date of the collected sample+the last four digits of the patient's hospitalization number. For example, if a sample was provided on Jan. 1, 2018 and the patient's hospitalization number was T001512765, the experiment number of the sample was 201801012765.

4. During operation, surgeons collected fresh samples in a sterile environment of an operating room and placed same in the prepared sample preservation solution (Table 1). The samples were temporarily preserved on ice after being isolated, and transported to a laboratory within two hours for next operation.

Embodiment 3. Treatment of Colorectal Cancer Solid Tumor Tissue Samples Before Dissociation The following operations were performed on ice, and the entire operation steps were completed within 10 minutes.

The surgical equipment used in the following operations was sterilized in advance at a high temperature and under a high pressure, and can be used after drying.

1. Weighing of samples.

2. Surfaces of the samples were washed with 75% (volume percentage) ethanol for 10 to 30 seconds.

3. The samples were washed 10 times with the sample washing solution (Table 2) and 5 times with a sterile PBS solution.

4. Adipose tissues, connective tissues, and necrotic tissues in the samples were carefully peeled off with equipment such as ophthalmic scissors, ophthalmic tweezers, and scalpels.

Embodiment 4. Dissociation of Colorectal Cancer Solid Tumor Tissue Samples

The surgical equipment used in the following embodiment was sterilized in advance at a high temperature and under a high pressure, and can be used after drying.

1. Tissues were cut into small pieces of about 1 mm$^3$ with ophthalmic scissors.

2. According to an amount of 0.1 mL of the sample dissociation solution (Table 3) per mg of tissues, the cut tissue samples were treated with the sample dissociation solution preheated at 37° C., and dissociated at 37° C. for 15 minutes to 3 hours. The dissociation of the samples was observed under a microscope every 15 minutes until a large number of single cells were observed.

3. The dissociation reaction was stopped with 10 times the volume of the dissociation stop solution (Table 8), and a cell suspension was collected.

4. The cell suspension was filtered with a 40 μm sterile cell strainer to remove tissue debris and adherent cells.

5. 800 g was centrifuged at room temperature for 10 minutes, and the supernatant was discarded.

6. Cells were re-suspended with 5 mL of a sterile PBS, 800 g was centrifuged at room temperature for 10 minutes, and the supernatant was discarded.

7. The cell precipitate was re-suspended with the colorectal cancer solid tumor primary cell medium (Table 9), cell statuses were observed under a microscope, and cells were counted.

As shown in FIG. 1, in the single cell suspension obtained by dissociation, in addition to tumor cells, there were also a large number of other cells of various types, such as red blood cells, lymphocytes, and fibrocytes. One of the advantages of this method was that in the subsequent culture process, only the cancer cells can be expanded in a large amount, while other cells gradually decreased or even disappeared, and finally high-purity colorectal cancer primary tumor cells were obtained.

Embodiment 5. Culture of Colorectal Cancer Solid Tumor Primary Cells

1. Suspension culture was performed on the colorectal cancer primary cells by using a low-attachment-surface. The medium used was the colorectal cancer solid tumor primary cell medium (Table 9) in Embodiment 1. Taking a six-pore plank as an example, the cells were planked with a density of $10^6$ cells per pore and cultured in a cell incubator at 37° C. and 5% $CO_2$.
2. Cell states were observed every day, and the medium was changed every 3 days until the cells formed masses with a diameter of about 80 μm.

Figure 2:
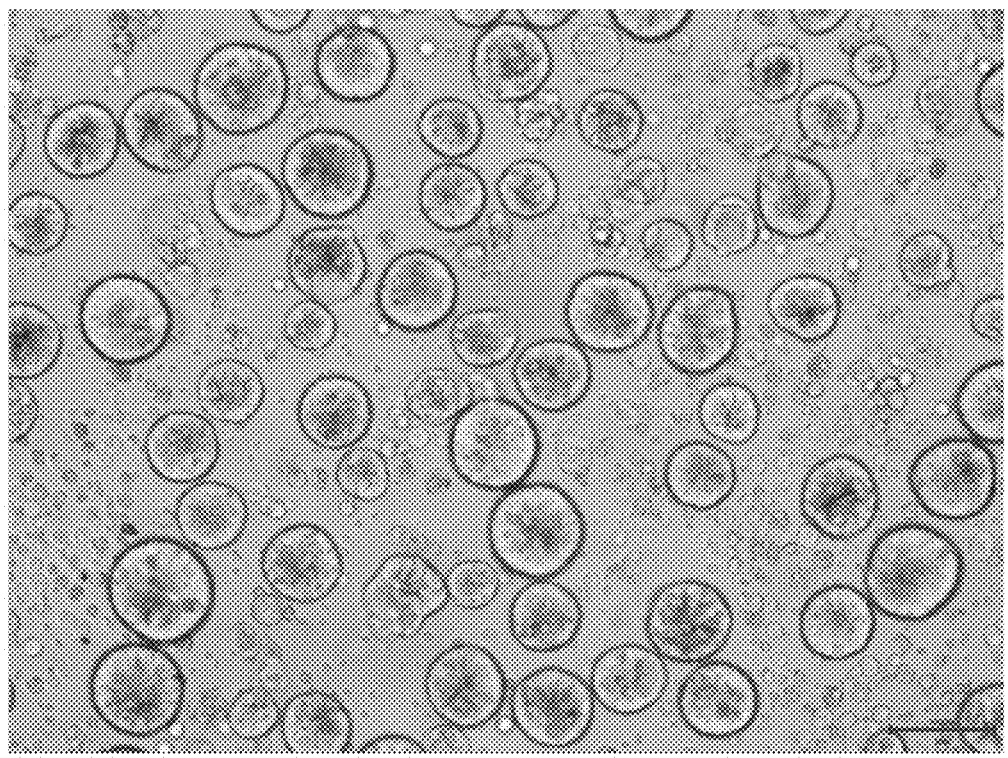
FIG. 2 shows cell masses obtained after primary culture of colorectal cancer tissues. The scale is 100 µm, 100 times magnification.

As shown in FIG. 2, after 3-10 days of culture, the cancer cells were expanded in a large amount to form cell masses with a diameter of 80 μm. The total number of the tumor cells can exceed $10^7$, and other types of cells were significantly reduced or even disappeared. This method has been tested on a large number of samples, showing that the success rate of in vitro culture of the colorectal cancer solid tumor primary tumor cells can reach 80%.

Embodiment 6. Passage of Colorectal Cancer Solid Tumor Primary Cells

1. Cell masses in a culture dish were collected, 800 g was centrifuged at room temperature for 10 minutes, and the supernatant was discarded.
2. The cell masses were washed with a sterile PBS solution, 800 g was centrifuged at room temperature for 10 minutes, and the supernatant was discarded.
3. The cell masses were re-suspended with the cell dissociation solution (Table 7) and dissociated at 37° C. The dissociation of the cell masses was observed under a microscope every 5 minutes, until the cell masses were dissociated into individual cells.
4. The dissociation reaction was stopped with 10 times the volume of the dissociation stop solution (Table 8), and a cell suspension was collected.
5. 800 g was centrifuged at room temperature for 10 minutes, and the supernatant was discarded.
6. The cell precipitate was re-suspended with the colorectal cancer solid tumor primary cell medium (Table 9), and cells were counted.
7. The colorectal cancer primary cells were cultured by using a low-attachment-surface. The medium used was the colorectal cancer solid tumor primary cell medium (Table 9) in Embodiment 1. Taking a six-pore plank as an example, the cells were planked with a density of $10^6$ cells per pore and cultured in a cell incubator at 37° C. and 5% $CO_2$.

Embodiment 7. Cryopreservation of Colorectal Cancer Solid Tumor Primary Cells

The colorectal cancer solid tumor primary cells subjected to the suspension culture can be cryopreserved after 2-3 passaging expansions:
1. Cell masses in a culture dish were collected, 800 g was centrifuged at room temperature for 10 minutes, and the supernatant was discarded.
2. The cell masses were washed with a sterile PBS solution, 800 g was centrifuged at room temperature for 10 minutes, and the supernatant was discarded.
3. The cell masses were re-suspended with the cell dissociation solution (Table 7) and dissociated at 37° C. The dissociation of the cell masses was observed under a microscope every 15 minutes, until the cell masses were dissociated into individual cells.
4. The dissociation reaction was stopped with 10 times the volume of the dissociation stop solution (Table 8), a cell suspension was collected, and cells were counted.
5. 800 g was centrifuged at room temperature for 10 minutes, and the supernatant was discarded.
6. The cell precipitate was re-suspended with the cell cryopreservation solution (Table 22) according to a density of $10^6$ cells/mL, and the cell suspension was dispensed in 2 mL cryopreservation tubes according to 1 ml of the cell suspension per tube, cryopreserved with a gradient cooling box overnight and then transferred to liquid nitrogen for long-term preservation.

Embodiment 8. Resuscitation of Colorectal Cancer Solid Tumor Primary Cells

The colorectal cancer solid tumor primary cells preserved in the liquid nitrogen can be resuscitated:
1. 37° C. sterile water was prepared five minutes in advance.
2. The cryopreservation tube was taken out of the liquid nitrogen, and the cells were quickly thawed in the 37° C. sterile water.
3. 800 g was centrifuged at room temperature for 10 minutes, and the supernatant was discarded.
4. The cell precipitate was re-suspended with the colorectal cancer solid tumor primary cell medium (Table 9), the colorectal cancer primary cells were cultured by using a low-attachment-surface, each tube of the cells was resuscitated to a 3.5 cm culture dish, and the cells were cultured in a cell incubator at 37° C. and 5% $CO_2$.

Embodiment 9. HE Staining Identification of Colorectal Cancer Solid Tumor Primary Cells Description of reagent consumables used in the following embodiment:
HE staining kit (Beijing SOLARBIOR Science & Technology Co., Ltd., #G1120):
Cationic anti-dropping slide (Beijing ZSGB™-Bio Co., Ltd.):
Xylene, methanol, acetone (Beijing Chemical Reagent Company, analytically pure);
Neutral resin glue (Beijing Yili Fine Chemical Co., Ltd.).
1. 800 g of a cell suspension were centrifuged, cells were collected, and cultured with the colorectal cancer ascites primary tumor cell medium (Table 9, where a final concentration of the human recombinant protein EGF was 20 ng/mL: a final concentration of the human recombinant protein bFGF was 20 ng/ml: a final concentration of the human recombinant protein HGF was 10 ng/ml: a final concentration of the human recombinant protein Wnt-3a was 200 ng/mL: a final concentration of the human recombinant protein Noggin was 100 ng/mL: a final concentration of the SB202190 was 10 μM: a final concentration of the A83-01 was 1 μM: a final concentration of the N-acetyl-L-cysteine was 1 mM: a final concentration of the Nicotinamide was 10 mM: a final concentration of the cortisol was 20 ng/mL: a final concentration of the Y-27632 was 10 μM) to obtain suspended colorectal cancer solid tumor primary cell masses, and the cell masses were immobilized with 4% paraformaldehyde. The cell mass precipitate was embedded in paraffin and sectioned with a thickness of 5 μm.

2. The paraffin sections were soaked in a xylene solution and incubated at room temperature for 5 minutes to remove the paraffin, and after 3 times, the sections were rinsed twice with deionized water.

3. The sections were immersed in absolute ethanol and incubated at room temperature for 10 minutes, and this process was repeated twice.

4. Ginger sections were immersed in 95% ethanol and incubated at room temperature for 10 minutes, and after twice, the sections were rinsed twice with deionized water.

5. When the water on the slide was slightly dry, 100 μL of hematoxylin staining solution was added for staining 1 minute.

6. The hematoxylin staining solution was sucked away, and the slide was washed with tap water 3 times.

7. 100 μL of differentiation solution was dripped for differentiating 1 minute.

8. The differentiation solution was sucked away, and the slide was sequentially washed twice with tap water and once with distilled water.

9. The water on the surface of the slide was sucked away, and 200 μL of cosin staining solution was added for staining 40 seconds.

10. The cosin staining solution was sucked away, and the slide was sequentially rinsed with 75%, 80%, 90%, and 100% ethanol and dewatered for 20 seconds, 20 seconds, 40 seconds, and 40 seconds.

11. After the ethanol was dry, 50 μL of xylene was dripped for cell permeation.

12. After the xylene was completely dry, a drop of neutral resin glue was dripped, the slide was sealed with a cover glass, the cells were observed under a microscope and pictures were taken.

Figure 3:
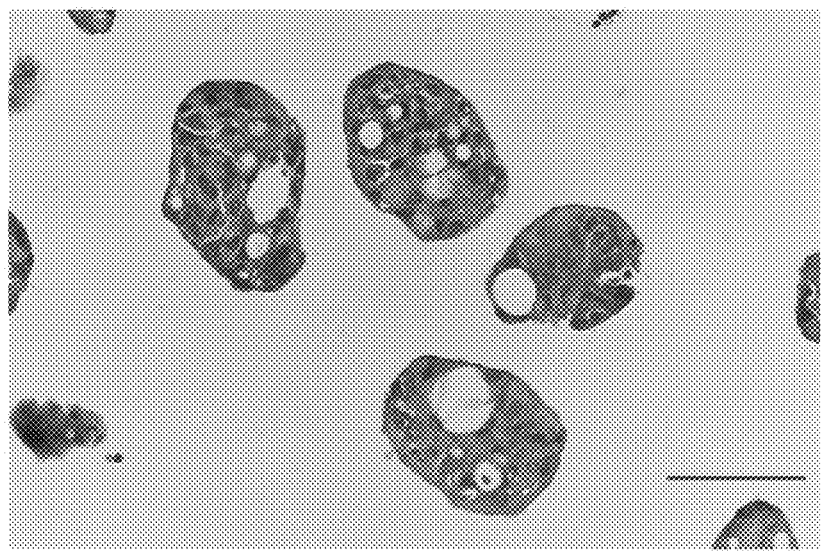
FIG. 3 shows an HE staining map of a colorectal cancer cell mass section obtained after primary culture of colorectal cancer tissues. The scale is 100 µm, 200 times magnification.

FIG. 3 shows an HE staining effect map of colorectal cancer solid tumor primary tumor cells cultured in vitro. It can be seen that these cells generally had cancer cell characteristics such as high nuclear-cytoplasmic ratio, dark nuclear staining, intranuclear chromatin agglutination, multinucleation, and uneven cell size, and dozens to hundreds of tumor cells aggregated to form tumor cell masses with certain three-dimensional structures.

Embodiment 10. Immunofluorescent Staining Identification of Colorectal Cancer Solid Tumor Primary Cells Description of reagents used in the following embodiment:

Paraformaldehyde (Beijing Chemical Reagent Company, analytically pure), paraformaldehyde powder was dissolved in ultra-pure water to prepare a 4% (4 g/100) mL) paraformaldehyde solution:

Methanol, dimethyl sulfoxide (Beijing Chemical Reagent Company; analytically pure):

Hydrogen peroxide (Beijing Chemical Reagent Company, 35%);

Methanol, dimethyl sulfoxide, and 35% hydrogen peroxide were mixed in a ratio of 4:4:1 (volume ratio) to prepare a DANCLANIM rinsing solution:

Bovine serum albumin (SIGMA®, #A1933), the bovine serum albumin was dissolved in a PBS solution to prepare a 3% (3 g/100) mL) BSA solution:

Immunofluorescent primary antibody (ABCAM®, #ab17139);

Immunofluorescent secondary antibody (CSTR, #4408):

Hoechst staining solution (Beijing SOLARBIOR Science & Technology Co., Ltd., #C0021):

Immunofluorescent staining was performed on the colorectal cancer solid tumor primary cell masses cultured with the colorectal cancer ascites primary tumor cell medium (Table 9, where the final concentration of the human recombinant protein EGF was 20 ng/ml: the final concentration of the human recombinant protein bFGF was 20 ng/mL: the final concentration of the human recombinant protein HGF was 10 ng/ml: the final concentration of the human recombinant protein Wnt-3a was 200 ng/ml: the final concentration of the human recombinant protein Noggin was 100 ng/ml; the final concentration of the SB202190 was 10 μM: the final concentration of the A83-01 was 1 μM: the final concentration of the N-acetyl-L-cysteine was 1 mM: the final concentration of the Nicotinamide was 10 mM: the final concentration of the cortisol was 20 ng/ml; the final concentration of the Y-27632 was 10 μM) according to the following steps. The primary antibody was CK8+CK18, which characterized epithelial cells.

1. The cell masses in the culture dish were collected and washed once with a PBS, and the cell precipitate was re-suspended with 4% paraformaldehyde and immobilized at 4° C. overnight.

2. 800 g was centrifuged, the supernatant was discarded, and the cell precipitate was re-suspended with a pre-cooled methanol solution and placed on ice for 1 hour.

3. 800 g was centrifuged, the supernatant was discarded, and the cell precipitate was re-suspended with a DANCLAN rinsing solution and placed at room temperature for 2 hours.

4. 800 g was centrifuged, the supernatant was discarded, and the cells were washed sequentially with 75%, 50%, and 25% (volume percentage) methanol solutions diluted with a PBS for 10 minutes each time.

5. 800 g was centrifuged, the supernatant was discarded, and the cell precipitate was suspended with a 3% BSA solution and sealed at room temperature for 2 hours.

6. The primary antibody was diluted with a 3% BSA solution in a ratio of 1:500, the cell precipitate was re-suspended with the antibody diluent (3% BSA solution), and the primary antibody was placed at 4° C. overnight.

7. 800 g was centrifuged, the supernatant was discarded, and the cell precipitate was washed with a PBS solution 5 times, 20 minutes each time.

8. The secondary antibody was diluted with a 3% BSA solution in a ratio of 1:2,000, the cell precipitate was re-suspended with the antibody diluent (3% BSA solution), and the secondary antibody was placed at room temperature for 2 hours.

9. 800 g was centrifuged, the supernatant was discarded, and the cell precipitate was washed with a PBS solution 5 times, 20 minutes each time.

10. A 100× Hoechst staining solution was added in a volume ratio of 1/100, and staining was performed at room temperature for 20 minutes.

11. The cell precipitate was washed twice with a PBS solution for 10 minutes each time. The staining of the cell masses was observed with a laser confocal microscope.

Figure 4:
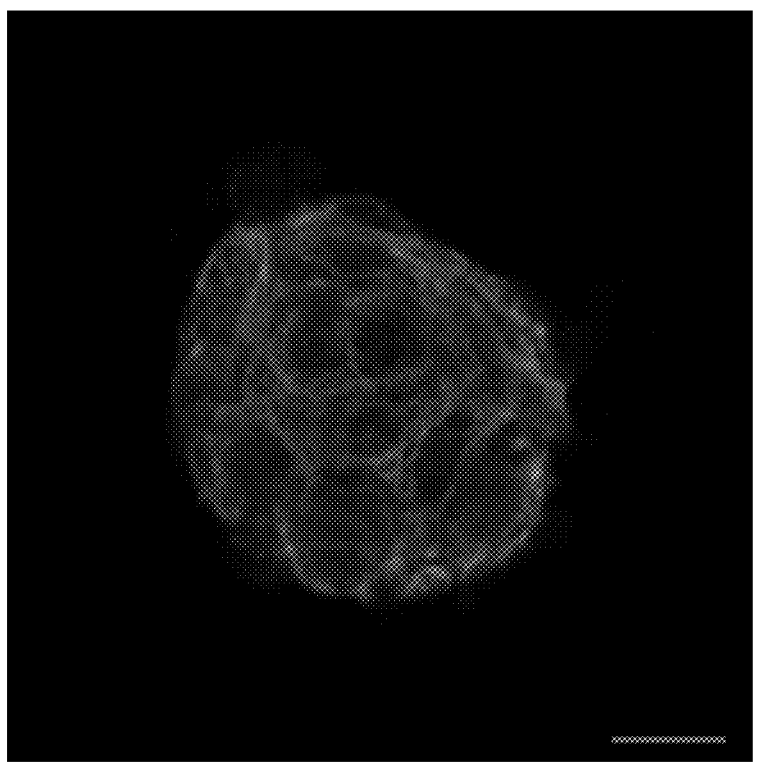
FIG. 4 shows an immunofluorescent staining map of cancer cell masses obtained after primary culture of colorectal cancer tissues. The scale is 50 µm, 200 times magnification.

FIG. 4 shows an immunofluorescent staining effect map of colorectal cancer solid tumor primary tumor cell masses cultured in vitro. It can be seen that the cells constituting the cell masses were all CK8/CK18 positive and were of epithelial origin, which confirmed that highly pure tumor cells were obtained by this culture method. The primary cultures of 20 colorectal cancer samples were identified by immunofluorescent staining. The statistical results showed that the proportion of tumor cells among the colorectal cancer solid tumor primary cells obtained by this method reached 72%-95% (Table 24).

TABLE 24

Immunofluorescent staining identification
of primary cultures of colorectal cancer samples

| Serial number | Sample number | CK8/CK18 positive rate |
|---|---|---|
| 1 | 20170613FDZ5181 | 84.5% |
| 2 | 20170613ZPW3709 | 85.5% |
| 3 | 20170623QJS8039 | 87.5% |
| 4 | 20170627GYL9278 | 93.9% |
| 5 | 20170627XHH2582 | 79.0% |
| 6 | 20170627XHH2582 | 74.5% |
| 7 | 20170628SY6545 | 83.6% |
| 8 | 20170711JP8251 | 89.5% |
| 9 | 20170719LWH7572 | 83.6% |
| 10 | 20170720YXL2334 | 73.5% |
| 11 | 20170721DZK0501 | 78.6% |
| 12 | 20170726GYJ1907 | 87.0% |
| 13 | 20170807WH1465 | 89.7% |
| 14 | 20170822HMR2096 | 88.0% |
| 15 | 20170828LYJ7774 | 83.0% |
| 16 | 20170830GXJ6131 | 80.2% |
| 17 | 20170905LJY4875 | 88.9% |
| 18 | 20170912XZG1390 | 90.8% |
| 19 | 20170926ZCL9071 | 72.2% |
| 20 | 20171010SJ9221 | 85.1% |

Embodiment 11. Primary Cell Cultures and Primary Tumor Tissues of Colorectal Cancer Solid Tumors The DNA extraction process mentioned in the following embodiment was performed by means of a Tiangen blood/tissue/cell genome extraction kit (DP304).

The library building process mentioned in the following embodiment was performed by means of an NEB DNA sequencing library building kit (E7645).

The high-throughput sequencing mentioned in the following embodiment referred to an Illumina HiSeq X-ten sequencing platform.

1. Colorectal cancer solid tumor samples were taken, 10 mg of a colorectal cancer solid tumor sample was first taken for DNA extraction, library building and whole genome high-throughput sequencing (WGS) with a sequencing depth of 30X before in vitro culture operation, and the remaining solid tumor samples were used for in vitro culture of colorectal cancer primary cells.

2. After colorectal cancer tissues were treated and cultured for a period of time, cell masses with a diameter of more than 80 pun were formed and recorded as P0 generation cells, and then recorded as P1, P2, . . . , Pn according to the number of passages. $10^6$ cells were taken from each of the P1, P2, P3, and P4 generations of colorectal cancer primary tumor cell cultures for DNA extraction, library building and whole genome high-throughput sequencing (WGS) with a sequencing depth of 30X.

Figure 5:
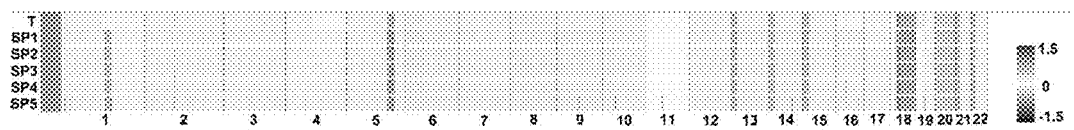
FIG. 5 shows that copy number variations of colorectal cancer primary cell cultures of respective generations (P1, P2, P3, P4, P5) and primary colorectal cancer tumor tissues (Tumor) are highly identical after copy number variation (CNV) analysis according to sequencing results.

3. Copy number variation (CNV) analysis was performed on each group of sequencing results to compare copy number variations between the primary colorectal cancer tumor tissues and the colorectal cancer primary cell cultures of respective generations. As shown in FIG. 5, the copy number variations of the colorectal cancer solid tumor primary cell cultures of respective generations (P1, P2, P3, P4, P5) were highly consistent with the copy number variation of the primary colorectal cancer tumor tissues (Tumor), so the colorectal cancer solid tumor primary cells obtained by this method can represent the truth of patient's primary tumors.

Embodiment 12. Comparison of success rates of culturing colorectal cancer solid tumor primary cells with different primary cell culture media In this embodiment, the operation method and process of primary culture of all samples were completely the same (refer to the above), and only the formulas of the culture media were different. The various primary cell culture media for testing were shown in Table 25. The scheme D was the formula used in the present invention, and details were shown in Table 9.

TABLE 25

Formulas of primary cell culture media for testing (100 mL)

| Culture medium | Reagent | Brand number | Amount | Final concentration |
|---|---|---|---|---|
| Scheme A | mTeSR ™ 1 medium | STEMCELL ™ #05850 | 100 mL | |
| Scheme B | Alveolar Epithelial Cell Medium | SCIENCELL ™ #3201 | 100 mL | |
| Scheme C | Double antibodies P/S | GIBCO ® #15140122 | 1 mL | 1% |
| | HEPES | GIBCO ® #15630080 | 1 mL | 10 mM |
| | 1,000× human recombinant protein EGF | 1,000× stock solution | 250 μL | 50 ng/ml |
| | 1,000× human recombinant protein bFGF | 1,000× stock solution | 100 μL | 20 ng/ml |
| | DMEM/F12 medium | GIBCO ® #14170161 | Made up to 100 mL | |
| Scheme D | See Table 9 | | | |

After preparation, the primary cell culture media were filtered and sterilized with a 0.22 μM syringe filter (MILLIPORE® SLGP033RS), and can be preserved at 4° C. for two weeks.

Each of the four primary cell medium schemes treated 20 colorectal cancer solid tumor tissue samples. Sample treatment and culture operations were performed according to the methods described in Embodiments 3, 4, and 5. After culture for 10 days, the success rates of colorectal cancer solid tumor primary cell culture were counted as shown in Table 26:

TABLE 26

Culture statuses of different culture media

| Primary cell medium scheme | Culture success rate |
|---|---|
| Scheme A | 0% (0/20) |
| Scheme B | 10% (2/20) |
| Scheme C | 20% (4/20) |
| Scheme D | 80% (16/20) |

It can be seen that the primary cell culture media had a great impact on the success rate of colorectal cancer primary cell culture, and the colorectal cancer solid tumor primary cell medium (Table 9) used in the present invention can stimulate the proliferation of cancer cells in the colorectal cancer solid tumor tissue samples to the greatest extent and improve the success rate of colorectal cancer solid tumor primary cell culture.

Embodiment 13. Comparison of Success Rates of Culturing Colorectal Cancer Solid Tumor Primary Cells with Different Sample Preservation Solutions In this embodiment, the operation method and process of primary culture of all samples were completely the same (refer to the above), and only the formulas of the sample preservation solutions were different. The various sample preservation solutions for testing were shown in Table 27. The scheme E was the formula used in the present invention, and details were shown in Table 1.

TABLE 27

Formulas of sample preservation solutions for testing (100 mL)

| Sample preservation solution Scheme | Reagent | Brand number | Amount | Final concentration |
|---|---|---|---|---|
| Scheme A | HBSS | GIBCO ® #14170161 | 100 mL | |
| Scheme B | Double antibodies P/S | GIBCO ® #15140122 | 1 mL | 1% |
| | HBSS | GIBCO ® #14170161 | Made up to 100 mL | |
| Scheme C | Double antibodies P/S | GIBCO ® #15140122 | 1 mL | 1% |
| | DMEM | GIBCO ® #11965-092 | Made up to 100 mL | |
| Scheme D | Ternary antibacterial and antifungal agent | GIBCO ® #15240062 | 1 mL | 1% |
| | Fetal bovine serum | GIBCO ® #16000-044 | 10 mL | 10% |
| | DMEM | GIBCO ® #11965-092 | Made up to 100 mL | |
| Scheme E | See Table 1 | | | |

After preparation, the various sample preservation solutions in the above table were dispensed in 15 mL centrifuge tubes, 5 mL per tube. The sample preservation solutions can be preserved at 4° C. for 1 month after being dispensed.

Each of the five sample preservation solution schemes treated 20 colorectal cancer solid tumor samples. The samples were temporarily preserved in the sample preservation solutions at 4° C. after being isolated. After the samples were isolated for 2 hours, sample treatment and culture operations were performed according to the methods described in Embodiments 3, 4, and 5. After culture for 10 days, the success rates of colorectal cancer solid tumor primary cell culture were counted as shown in Table 28:

TABLE 28

Culture statuses of different sample preservation solutions

| Sample preservation solution | Culture success rate | Bacteria/fungi contamination rate |
|---|---|---|
| Scheme A | 30% (6/20) | 75% (15/20) |
| Scheme B | 55% (11/20) | 15% (3/20) |
| Scheme C | 60% (12/20) | 20% (4/20) |
| Scheme D | 75% (15/20) | 0% (0/20) |
| Scheme E | 80% (16/20) | 0% (0/20) |

It can be seen that the formulas of the sample preservation solutions had a great impact on the success rate of colorectal cancer solid tumor primary cell culture, and the sample preservation solution (Table 1) used in the present invention can protect the activity of cancer cells in the colorectal cancer solid tumor tissue samples to the greatest extent, and improve the success rate of culture.

Embodiment 14. Comparison of Success Rates of Culturing Colorectal Cancer Solid Tumor Primary Cells with Different Sample Dissociation Solutions In this embodiment, the operation method and process of primary culture of all samples were completely the same (refer to the above), and only the formulas of the sample dissociation solutions were different. The various sample dissociation solutions for testing were shown in Table 29. The scheme D was the formula used in the present invention, and details were shown in Table 3.

TABLE 29

Formulas of sample dissociation solutions for testing (10 mL)

| Sample dissociation solution | Reagent | Brand number | Amount | Final concentration |
|---|---|---|---|---|
| Scheme A | Trypsin | GIBCO ® #25200056 | 10 mL | |
| Scheme B | 0.5M EDTA | INVITROGEN ® #AM9261 | 10 μL | 5 mM |
| | DNAse | THERMO ® #EN0521 | 62.5 μL | 62.5 U/mL |
| | TrypLE ™ Express | GIBCO ® #12604013 | Made up to 10 mL | |
| Scheme C | 20× collagenase IV | 20× stock solution | 1 mL | 200 U/mL |
| | DNAse | THERMO ® #EN0521 | 62.5 μL | 62.5 U/mL |
| | PBS | GIBCO ® #21-040-CVR | Made up to 10 mL | |
| Scheme D | See Table 3 | | | |

The sample dissociation solutions were prepared for current use.

20 samples of colorectal cancer solid tumor tissue blocks with a weight of more than 100 mg were selected, averagely divided into four parts, and respectively treated and cultured with the above-mentioned four sample dissociation solutions according to the methods described in Embodiments 3, 4, and 5. After culture for 10 days, the success rates of colorectal cancer solid tumor primary cell culture were counted as shown in Table 30:

TABLE 30

Culture statuses of different sample dissociation solutions

| Serial number | Sample number | Scheme A | Scheme B | Scheme C | Scheme D |
|---|---|---|---|---|---|
| 1 | 20170621HYF0118 | Failure | Failure | Success | Success |
| 2 | 20170627LSX2279 | Failure | Success | Success | Success |
| 3 | 20170627SXL9673 | Failure | Failure | Failure | Success |
| 4 | 20170628ZSQ7313 | Failure | Success | Success | Success |
| 5 | 20170629YZY3072 | Failure | Failure | Failure | Success |
| 6 | 20170629GLR1929 | Failure | Failure | Failure | Failure |
| 7 | 20170707WY9660 | Failure | Success | Success | Success |
| 8 | 20170717ZJ0831 | Failure | Failure | Failure | Success |
| 9 | 20170720GL0285 | Failure | Failure | Failure | Success |
| 10 | 20170726GXW4931 | Failure | Failure | Success | Success |
| 11 | 20170727MJC5252 | Failure | Failure | Success | Success |
| 12 | 20170801LQS1498 | Failure | Success | Success | Success |
| 13 | 20170807ZJZ9161 | Failure | Success | Success | Success |
| 14 | 20170808ZFG8438 | Failure | Failure | Failure | Failure |

TABLE 30-continued

Culture statuses of different sample dissociation solutions

| Serial number | Sample number | Scheme A | Scheme B | Scheme C | Scheme D |
|---|---|---|---|---|---|
| 15 | 20170810LSL0445 | Failure | Failure | Failure | Failure |
| 16 | 20170810WJ5078 | Failure | Failure | Failure | Success |
| 17 | 20170816ZBH6938 | Success | Success | Success | Success |
| 18 | 20170821GY0193 | Failure | Failure | Failure | Success |
| 19 | 20170828WYQ1401 | Failure | Failure | Success | Success |
| 20 | 20170904ZQR5422 | Failure | Failure | Success | Success |
| | Summary | 5% (1/20) | 25% (6/20) | 55% (9/20) | 85% (17/20) |

It can be seen that the formulas of the sample dissociation solutions had a great impact on the success rate of colorectal cancer solid tumor primary cell culture, and the sample dissociation solution (Table 3) used in the present invention can dissociate cancer cells in the colorectal cancer solid tumor tissues to the greatest extent, and improve the success rate of colorectal cancer solid tumor primary cell culture.

Embodiment 15. Comparison of Success Rates of Passing Colorectal Cancer Solid Tumor Primary Cells with Different Cell Dissociation Solutions In this embodiment, the operation method and process of primary cell passage of all samples were completely the same (refer to the above), and only the formulas of the cell dissociation solutions were different. The various cell dissociation solutions for testing were shown in Table 31. The scheme D was the formula used in the present invention, and details were shown in Table 7.

TABLE 31

Formulas of cell dissociation solutions for testing (10 mL)

| Cell dissociation solution | Reagent | Brand number | Amount | Final concentration |
|---|---|---|---|---|
| Scheme A | Trypsin | GIBCO ® #25200056 | 10 mL | |
| Scheme B | 0.5M EDTA | INVITROGEN ® #AM9261 | 10 μL | 5 mM |
| | TrypLE ™ Express | GIBCO ® #12604013 | Made up to 10 mL | |
| Scheme C | 10× collagenase I | 10× stock solution | 1 mL | 200 U/mL |
| | 10× collagenase II | 10× stock solution | 1 mL | 200 U/mL |
| | 20× collagenase IV | 20× stock solution | 0.5 mL | 100 U/mL |
| | PBS | GIBCO ® #21-040-CVR | Made up to 10 mL | |
| Scheme D | See Table 7 | | | |

The cell dissociation solutions were prepared for current use.

20 colorectal cancer solid tumor primary cell samples that had been successfully cultured were selected, and the cultured colorectal cancer solid tumor primary cells were continuously passaged with the above-mentioned four cell dissociation solutions according to the method described in Embodiment 6. When cancer cells expanded to form cell masses with a diameter of 80 μm, the cancer cells were passaged (not more than 10 times), and the maximum number of passages was recorded. The statistical results were shown in Table 32:

TABLE 32

Culture statuses of different cell dissociation solutions

| Serial number | Sample number | Scheme A | Scheme B | Scheme C | Scheme D |
|---|---|---|---|---|---|
| 1 | 20170621HYF0118 | 1 | 2 | 5 | 8 |
| 2 | 20170623QJS8039 | 1 | 3 | 7 | 10 |
| 3 | 20170627GYL9278 | 1 | 3 | 5 | 10 |
| 4 | 20170627LSX2279 | 1 | 4 | 9 | 10 |
| 5 | 20170627SXL9673 | 1 | 5 | 5 | 10 |
| 6 | 20170627XHH2582 | 1 | 5 | 6 | 10 |
| 7 | 20170627XHH2582 | 1 | 3 | 6 | 8 |
| 8 | 20170628SY6545 | 1 | 2 | 8 | 8 |
| 9 | 20170628ZSQ7313 | 2 | 5 | 9 | 10 |
| 10 | 20170629GLR1929 | 1 | 5 | 6 | 8 |
| 11 | 20170629YZY3072 | 1 | 2 | 8 | 9 |
| 12 | 20170707WY9660 | 1 | 4 | 6 | 8 |
| 13 | 20170711JP8251 | 1 | 5 | 5 | 8 |
| 14 | 20170717ZJ0831 | 1 | 4 | 7 | 9 |
| 15 | 20170719LWH7572 | 1 | 5 | 7 | 10 |
| 16 | 20170720GL0285 | 1 | 5 | 7 | 9 |
| 17 | 20170720YXL2334 | 1 | 2 | 9 | 9 |
| 18 | 20170721DZK0501 | 1 | 3 | 9 | 10 |
| 19 | 20170726GXW4931 | 1 | 4 | 5 | 8 |
| 20 | 20170816ZBH6938 | 2 | 6 | 10 | 10 |
| Summary of possible passages | | 1-2 times | 2-6 times | 5-10 times | 8 times or more |

It can be seen that the formulas of the cell dissociation solutions had a great impact on the success rate of passage of the colorectal cancer solid tumor primary cells. The cell dissociation solution (Table 7) used in the present invention can gently dissociate cancer cells in the cell masses, so that the samples can be continuously passaged while maintaining the activity of the colorectal cancer solid tumor primary cells.

Embodiment 16. Preparation of Reagents for Culturing Colorectal Cancer Ascites Primary Tumor Cells 1. Cell Isolation Buffer (100 mL)

A specific formula of the cell isolation buffer (100 mL) was shown in Table 33:

TABLE 33

Cell isolation buffer (100 mL)

| Reagent | Brand number | Amount | Final concentration |
|---|---|---|---|
| Ternary antibacterial and antifungal agent | GIBCO ® #15240062 | 1 mL | 1% |
| 1,000× heparin sodium solution | 1,000× stock solution | 0.1 mL | 10 IU/mL |
| PBS | GIBCO ® #21-040-CVR | Made up to 100 mL | |

The cell isolation buffer can be preserved at 4° C. for 1 month after preparation.

In Table 33, the preparation of the heparin sodium solution was shown in Table 34.

TABLE 34

| 1,000× heparin sodium (1 mL) | | | |
|---|---|---|---|
| Reagent | Brand number | Amount | Final concentration |
| Heparin sodium | SOLARBIO ® #H8270 | 10 kIU | 10 kIU/mL |
| Ultra-pure water | | Made up to 1 mL | |

The 1,000× heparin sodium solution was prepared for current use.

2. Cell Dissociation Solution (10 mL)

A specific formula of the cell dissociation solution (10 mL) was shown in Table 7 (same as the formula of the cell dissociation solution used for colorectal cancer solid tumor primary cell culture).

3. Dissociation Stop Solution (100 mL)

A specific formula of the dissociation stop solution (100 mL) was shown in Table 8 (same as the formula of the dissociation stop solution used for colorectal cancer solid tumor primary cell culture).

4. Colorectal Cancer Ascites Primary Tumor Cell Medium (100 mL)

A specific formula of the colorectal cancer ascites primary tumor cell medium (100 mL) was shown in Table 9 (same as the formula of the colorectal cancer solid tumor primary cell medium used for colorectal cancer solid tumor primary cell culture).

5. Cell Cryopreservation Solution

A specific formula of the cell cryopreservation solution was shown in Table 22 (same as the formula of the cell cryopreservation solution used for colorectal cancer solid tumor primary cell culture).

Embodiment 17. Obtaining of Colorectal Cancer Ascites Samples

1. Cooperation with a top three hospital, the cooperation had passed the formal medical ethics review.

2. Attending physicians selected participating patients according to the clinical indications specified in the medical guidelines, and selected appropriate samples according to the intraoperative clinical indications for in vitro culture. The selection criteria for samples were: primary colorectal cancer, the pathological stage was stage IV, the pathological type was colorectal cancer or colorectal cancer metastasis lesion, the patients had malignant ascites required to be discharged, and the discharge volume was not less than 50 mL.

3. The attending physicians provided basic clinical information such as patient's gender, age, medical history, family history, smoking history, pathological stage type, and clinical diagnosis. Information related to patient's privacy, such as patient's name and ID number, was concealed and replaced with a uniform experiment number. The naming principle of the experiment number was the eight-digit date of the collected sample+the last four digits of the patient's hospitalization number. For example, if a sample was provided on Jan. 1, 2018 and the patient's hospitalization number was T001512765, the experiment number of the sample was 201801012765.

4. The attending physicians collected ascites samples with sterile equipment and vessels. The samples were temporarily preserved on ice after being isolated, and transported to a laboratory within 72 hours for next operation.

Embodiment 18. Pretreatment of Colorectal Cancer Ascites Samples

The following embodiment was operated on ice:

1. The colorectal cancer ascites samples were placed on ice for about 30 minutes, so that clots and large insoluble solids in the samples precipitated to bottoms of sample tubes.

2. The supernatant was carefully transferred to 50 mL sterile centrifuge tubes.

3. 2,000 g was centrifuged at normal temperature for 5 minutes, and the supernatant was discarded.

4. The cell precipitate was re-suspended with the cell isolation buffer (Table 33), 2,000 g was centrifuged at normal temperature for 5 minutes, and the supernatant was discarded.

5. The cell precipitate was re-suspended with the cell isolation buffer (Table 33), and the concentration of cells was adjusted to $10^7$-$10^8$ cells/mL.

Embodiment 19. Density Gradient Centrifugation of Colorectal Cancer Ascites Samples 1. A FICOLL cell isolation solution (MP™ #50494) with the same volume as the cell suspension was taken with a 50 mL sterile centrifuge tube.

2. The cell suspension was carefully added to the upper layer of the cell isolation solution to form a clear interface between the two.

3. 2,000 g was horizontally centrifuged at normal temperature for 20 minutes.

4. Albuginea in the middle layer was sucked into a new tube.

5. The cell precipitate was re-suspended with 20 mL of sterile PBS, 1,500 g was centrifuged at normal temperature for 10 minutes, and the supernatant was discarded.

6. The cell precipitate was re-suspended with the colorectal cancer ascites primary tumor cell medium (Table 9), cell statuses were observed under a microscope, and cells were counted.

Figure 6:
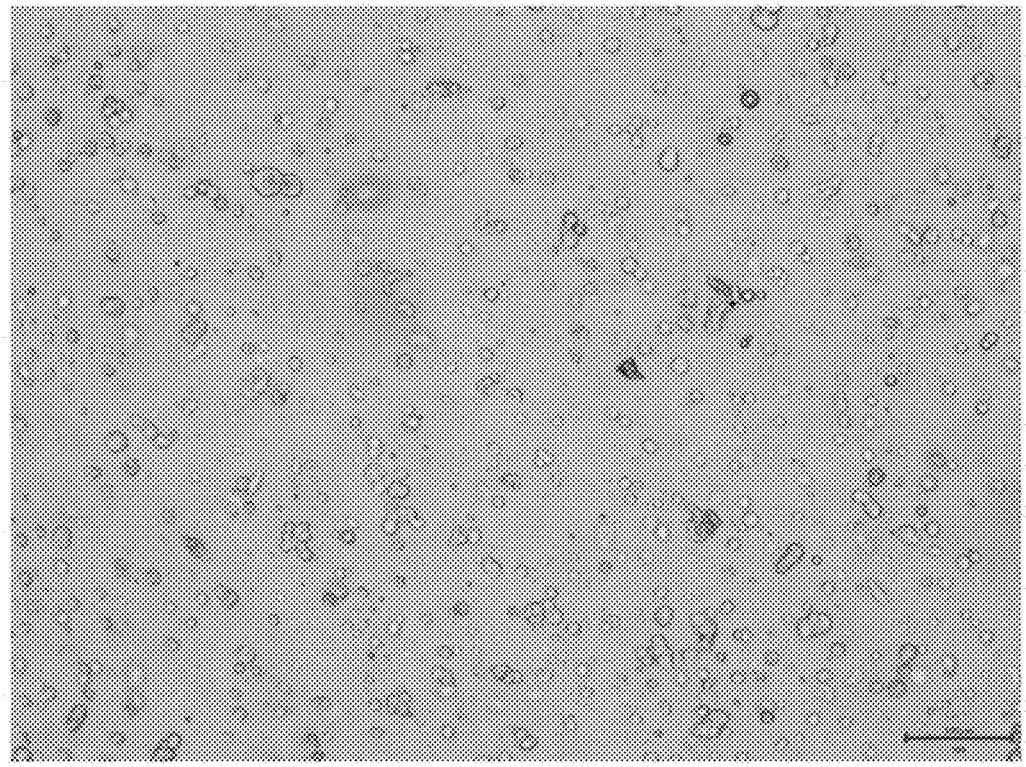
FIG. 6 shows single cells isolated from a colorectal cancer ascites sample. The scale is 100 µm.

As shown in FIG. 6, in the single cell suspension obtained by isolation from the colorectal cancer ascites samples, in addition to tumor cells, there were also a large number of other cells of various types, such as red blood cells, lymphocytes, and fibrocytes. One of the advantages of this method was that in the subsequent culture process, only the cancer cells can be expanded in a large amount, while other cells gradually decreased or even disappeared, and finally high-purity colorectal cancer primary tumor cells were obtained.

Embodiment 20. Culture of Primary Tumor Cells Derived from Colorectal Cancer Ascites 1. Suspension culture was performed on the colorectal cancer ascites primary tumor cells by using a low-attachment-surface. Taking a six-pore plank as an example, the cells were planked with a density of $10^6$ cells per pore and cultured in a cell incubator at 37° C. and 5% $CO_2$.

2. Cell statuses were observed every day, and the medium was changed every 3 days until the cells formed masses with a diameter of about 80 μm.

Figure 7:
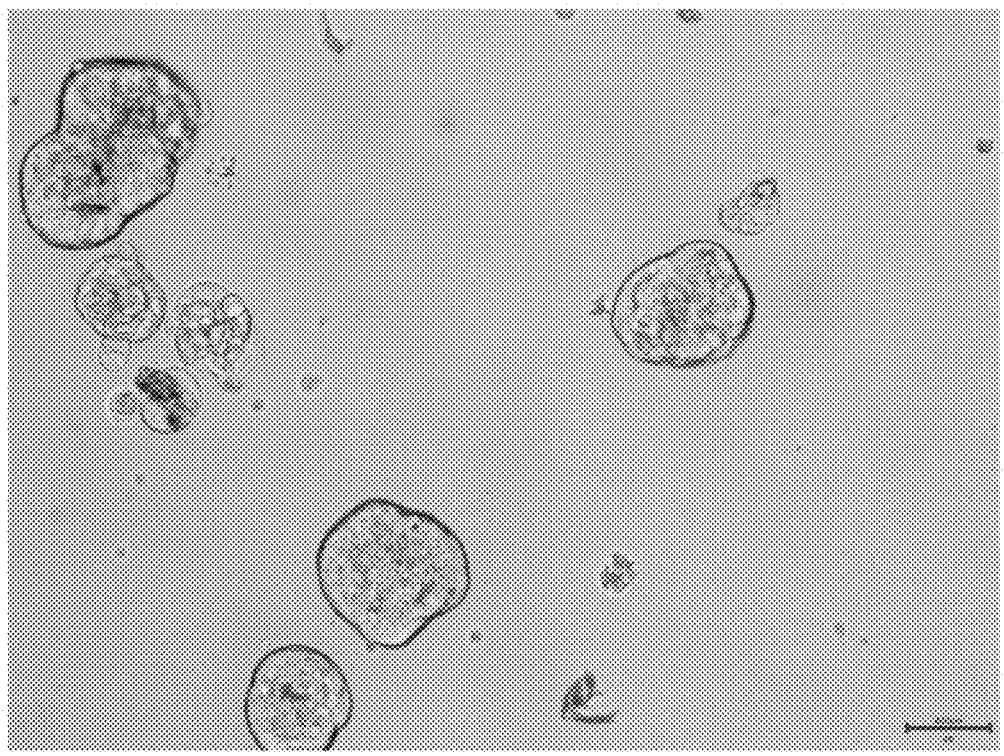
FIG. 7 shows cell masses obtained after culture of primary tumor cells in a colorectal cancer ascites sample. The scale is 200µ m.

As shown in FIG. 7, after 3-10 days of culture, the cancer cells were expanded in a large amount to form cell masses with a diameter of 80 μm. The total number of the tumor cells can exceed $10^7$, and other types of cells were significantly reduced or even disappeared. This method has been tested on a large number of samples, showing that the success rate of in vitro culture of the primary tumor cells derived from colorectal cancer ascites can reach 80%.

Embodiment 21. Passage of Primary Tumor Cells Derived from Colorectal Cancer Ascites 1. Cell masses in a culture dish were collected, 800 g was centrifuged at room temperature for 10 minutes, and the supernatant was discarded.
2. The cell masses were washed with a sterile PBS solution, 800 g was centrifuged at room temperature for 10 minutes, and the supernatant was discarded.
3. The cell masses were re-suspended with the cell dissociation solution (Table 7) and dissociated at 37° C. The dissociation of the cell masses was observed under a microscope every 5 minutes, until the cell masses were dissociated into individual cells.
4. The dissociation reaction was stopped with 10 times the volume of the dissociation stop solution (Table 8), and a cell suspension was collected.
5. 800 g was centrifuged at room temperature for 10 minutes, and the supernatant was discarded.
6. The cell precipitate was re-suspended with the colorectal cancer ascites primary tumor cell medium (Table 9), and cells were counted.
7. The colorectal cancer primary cells were cultured by using a low-attachment-surface. Taking a six-pore plank as an example, the cells were planked with a density of $10^6$ cells per pore and cultured in a cell incubator at 37° C. and 5% $CO_2$.

Embodiment 22. Cryopreservation of Primary Tumor Cells Derived from Colorectal Cancer Ascites The colorectal cancer ascites primary tumor cells subjected to the suspension culture can be cryopreserved after 2-3 passaging expansions:
1. Cell masses in a culture dish were collected, 800 g was centrifuged at room temperature for 10 minutes, and the supernatant was discarded.
2. The cell masses were washed with a sterile PBS solution, 800 g was centrifuged at room temperature for 10 minutes, and the supernatant was discarded.
3. The cell masses were re-suspended with the cell dissociation solution (Table 7) and dissociated at 37° C. The dissociation of the cell masses was observed under a microscope every 5 minutes, until the cell masses were dissociated into individual cells.
4. The reaction was stopped with 10 times the volume of the dissociation stop solution (Table 8), a cell suspension was collected, and cells were counted.
5. 800 g was centrifuged at room temperature for 10 minutes, and the supernatant was discarded.
6. The cell precipitate was re-suspended with the cell cryopreservation solution (Table 22) according to a density of $10^6$ cells/mL, and the cell suspension was dispensed in 2 mL cryopreservation tubes according to 1 ml of the cell suspension per tube, cryopreserved with a gradient cooling box overnight and then transferred to liquid nitrogen for long-term preservation.

Embodiment 23. Resuscitation of Primary Tumor Cells Derived from Colorectal Cancer Ascites The primary tumor cells derived from colorectal cancer ascites, preserved in the liquid nitrogen, can be resuscitated:

1. 37° C. sterile water was prepared five minutes in advance.
2. The cryopreservation tube was taken out of the liquid nitrogen, and the cells were quickly thawed in the 37° C. sterile water.
3. 800 g was centrifuged at room temperature for 10 minutes, and the supernatant was discarded.
4. The cell precipitate was re-suspended with the colorectal cancer ascites primary tumor cell medium (Table 9), the primary tumor cells derived from colorectal cancer ascites were cultured by using a low-attachment-surface, each tube of the cells was resuscitated to a 3.5 cm culture dish, and the cells were cultured in a cell incubator at 37° C. and 5% $CO_2$.

Embodiment 24. HE Staining Identification of Primary Tumor Cells Derived from Colorectal Cancer Ascites Description of reagent consumables used in the following embodiment:
HE staining kit (Beijing SOLARBIOR Science & Technology Co., Ltd., #G1120):
Cationic anti-dropping slide (Beijing ZSGB-Bio Co., Ltd.):
Xylene, methanol, acetone (Beijing Chemical Reagent Company, analytically pure):
Neutral resin gluc (Beijing Yili Fine Chemical Co., Ltd.).
1. A cell suspension with a concentration of 10+ cells/mL was prepared from suspended primary tumor cells derived from colorectal cancer ascites, which were cultured with the colorectal cancer ascites primary tumor cell medium (Table 9, where the final concentration of the human recombinant protein EGF was 20 ng/ml; the final concentration of the human recombinant protein bFGF was 20 ng/ml: the final concentration of the human recombinant protein HGF was 10 ng/mL: the final concentration of the human recombinant protein Wnt-3a was 200 ng/mL: the final concentration of the human recombinant protein Noggin was 100 ng/ml: the final concentration of the SB202190 was 10 µM: the final concentration of the A83-01 was 1 µM: the final concentration of the N-acetyl-L-cysteine was 1 mM: the final concentration of the Nicotinamide was 10 mM: the final concentration of the cortisol was 20 ng/ml: the final concentration of the Y-27632 was 10 µM), and 10 µL was dripped onto a cationic anti-dropping slide and dried naturally.
2. 50 µL of a mixed solution of methanol/acetone (volume ratio 1:1) pre-cooled at 4° C. was carefully dripped onto the air-dried cells, and then the slide was placed in a 4° C. refrigerator and immobilized for 10 minutes.
3. The slide with immobilized cells was taken out and dried naturally at room temperature.
4. The slide was washed twice with 200 µL of PBS.
5. When the water on the slide was slightly dry, 100 µL of hematoxylin staining solution was added for staining 1 minute.
6. The hematoxylin staining solution was sucked away, and the slide was washed with 200 µL of tap water 3 times.
7. 100 µL of differentiation solution was dripped for differentiating 1 minute.
8. The differentiation solution was sucked away, and the slide was sequentially washed twice with tap water and once with distilled water.
9. The water on the surface of the slide was sucked away, and 200 µL of eosin staining solution was added for staining 40 seconds.

10. The eosin staining solution was sucked away, and the slide was sequentially rinsed with 75%, 80%, 90%, and 100% ethanol and dewatered for 20 seconds, 20 seconds, 40 seconds, and 40 seconds.

11. After the ethanol was dry, 50 µL of xylene was dripped for cell permeation.

12. After the xylene was completely dry, a drop of neutral resin glue was dripped, the slide was sealed with a cover glass, the cells were observed under a microscope and pictures were taken.

Figure 8:
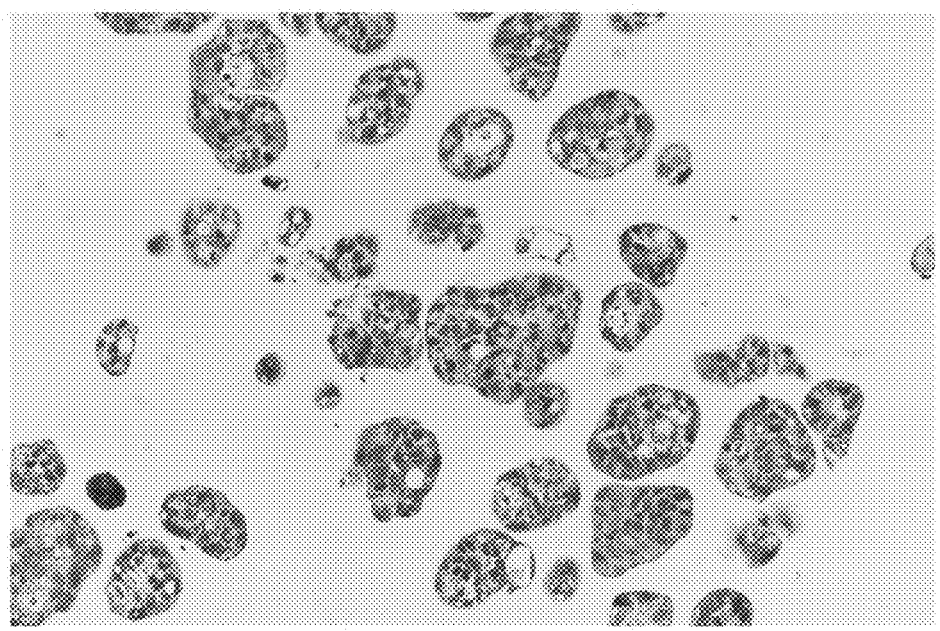
FIG. 8 shows an HE staining map of colorectal cancer cells obtained after primary culture of a colorectal cancer ascites sample.

FIG. 8 shows an HE staining effect map of primary tumor cells derived from colorectal cancer ascites cultured in vitro. It can be seen that these cells generally had cancer cell characteristics such as high nuclear-cytoplasmic ratio, dark nuclear staining, intranuclear chromatin agglutination, multinucleation, and uneven cell size.

Embodiment 25. Immunofluorescent Staining Identification of Primary Tumor Cells Derived from Colorectal Cancer Ascites Description of reagents used in the following embodiment:

Paraformaldehyde (Beijing Chemical Reagent Company, analytically pure), paraformaldehyde powder was dissolved in ultra-pure water to prepare a 4% paraformaldehyde solution:

Methanol, dimethyl sulfoxide (Beijing Chemical Reagent Company, analytically pure); Hydrogen peroxide (Beijing Chemical Reagent Company, 35%):

Methanol, dimethyl sulfoxide, and 35% hydrogen peroxide were mixed in a ratio of 4:4:1 to prepare a DANCLAN rinsing solution:

Bovine serum albumin (SIGMA, #A1933), the bovine serum albumin was dissolved in a PBS solution to prepare a 3% BSA solution;

Immunofluorescent primary antibody (ABCAM®, #ab17139);

Immunofluorescent secondary antibody (CSTR, #4408):

Hoechst staining solution (Beijing SOLARBIOR Science & Technology Co., Ltd., #C0021);

Immunofluorescent staining was performed on the colorectal cancer ascites derived primary tumor cell masses cultured with the colorectal cancer ascites primary tumor cell medium (Table 9, where the final concentration of the human recombinant protein EGF was 20 ng/mL: the final concentration of the human recombinant protein bFGF was 20 ng/mL: the final concentration of the human recombinant protein HGF was 10 ng/ml; the final concentration of the human recombinant protein Wnt-3a was 200 ng/mL: the final concentration of the human recombinant protein Noggin was 100 ng/ml: the final concentration of the SB202190 was 10 µM: the final concentration of the A83-01 was 1 µM: the final concentration of the N-acetyl-L-cysteine was 1 mM: the final concentration of the Nicotinamide was 10 mM: the final concentration of the cortisol was 20 ng/ml: the final concentration of the Y-27632 was 10 µM) according to the following steps. The primary antibody was CK8+CK18, which characterized epithelial cells.

1. The ascites derived primary tumor cell masses in the culture dish were collected and washed once with a PBS, and the cell precipitate was re-suspended with 4% paraformaldehyde and immobilized at 4° C. overnight.

2. 800 g was centrifuged, the supernatant was discarded, and the cell precipitate was re-suspended with a pre-cooled methanol solution and placed on ice for 1 hour.

3. 800 g was centrifuged, the supernatant was discarded, and the cell precipitate was re-suspended with a DANCLAN rinsing solution and placed at room temperature for 2 hours.

4. 800 g was centrifuged, the supernatant was discarded, and the cells were washed sequentially with 75%, 50%, and 25% methanol solutions diluted with a PBS for 10 minutes each time.

5. 800 g was centrifuged, the supernatant was discarded, and the cell precipitate was suspended with a 3% BSA solution and sealed at room temperature for 2 hours.

6. The primary antibody was diluted with a 3% BSA solution in a ratio of 1:500, the cell precipitate was re-suspended with the antibody diluent, and the primary antibody was placed at 4° C. overnight.

7. 800 g was centrifuged, the supernatant was discarded, and the cell precipitate was washed with a PBS solution 5 times, 20 minutes each time.

8. The secondary antibody was diluted with a 3% BSA solution in a ratio of 1:2,000, the cell precipitate was re-suspended with the antibody diluent, and the secondary antibody was placed at room temperature for 2 hours.

9. 800 g was centrifuged, the supernatant was discarded, and the cell precipitate was washed with a PBS solution 5 times, 20 minutes each time.

10. A 100× Hoechst staining solution was added in a volume ratio of 1/100, and staining was performed at room temperature for 20 minutes.

11. The cell precipitate was washed twice with a PBS solution for 10 minutes each time. The staining of the cell masses was observed with a laser confocal microscope.

Figure 9:
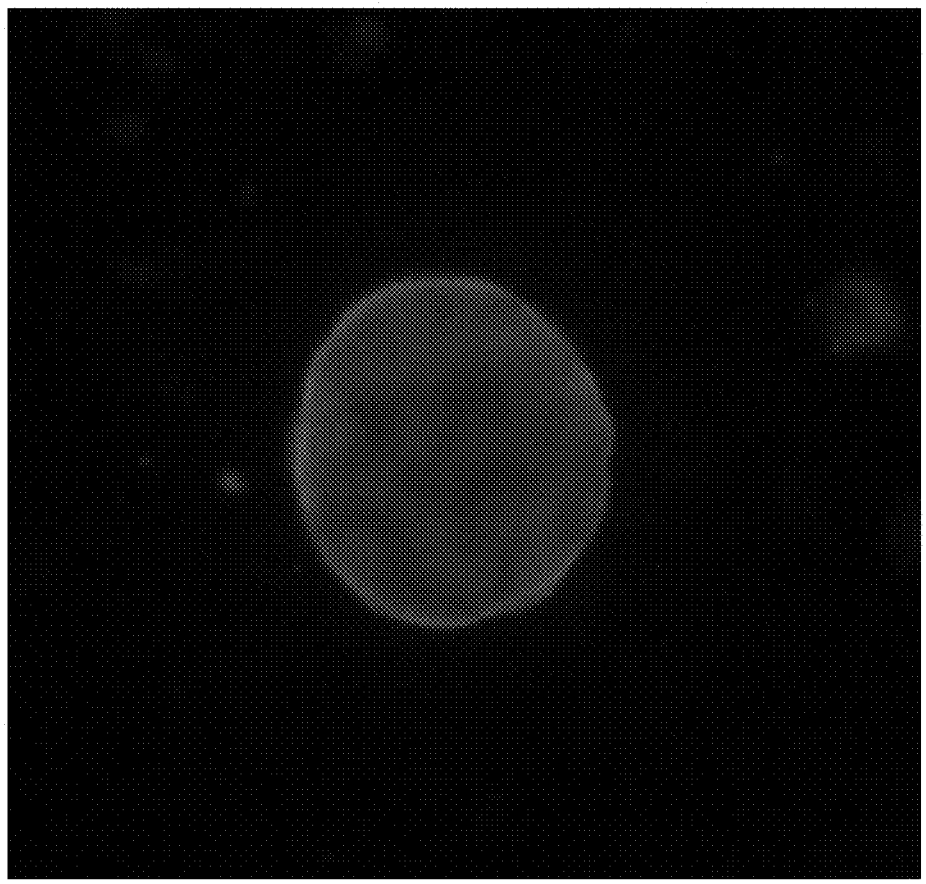
FIG. 9 shows an immunofluorescent staining map of cancer cell masses obtained after primary culture of a colorectal cancer ascites sample.

FIG. 9 shows an immunofluorescent staining effect map of colorectal cancer ascites derived primary tumor cell masses cultured in vitro. It can be seen that the cells constituting the cell masses were all CK8/CK18 positive and were of epithelial origin, which confirmed that highly pure tumor cells were obtained by this culture method. 20 colorectal cancer ascites primary cultures were identified by immunofluorescent staining. The statistical results showed that the proportion of tumor cells among the colorectal cancer ascites derived primary tumor cells obtained by this method reached 72%-91% (Table 35).

TABLE 35

Immunofluorescent staining identification of primary culture of colorectal cancer ascites

| Serial number | Sample number | CK8/CK18 positive rate |
|---|---|---|
| 1 | 20180722ZQH3005 | 86% |
| 2 | 20181217ZZY1386 | 84% |
| 3 | 20180530GW6307 | 78% |
| 4 | 20180522HC6914 | 76% |
| 5 | 20180508LY0054 | 74% |
| 6 | 20181106NLC6799 | 85% |
| 7 | 20180423CXC9250 | 87% |
| 8 | 20180423WFY4087 | 85% |
| 9 | 20180424ZZH5496 | 88% |
| 10 | 20181220WF2858 | 72% |
| 11 | 20181008JF4076 | 77% |
| 12 | 20180530FKX7348 | 78% |
| 13 | 20180703QWG0065 | 81% |
| 14 | 20180918JJB0734 | 75% |
| 15 | 20180531LWY1184 | 90% |
| 16 | 20181101LZY1263 | 77% |
| 17 | 20180713QZG1394 | 91% |
| 18 | 20180711DHD6099 | 80% |
| 19 | 20180716CL8052 | 74% |
| 20 | 20180702QCF9653 | 86% |

Embodiment 26. Colorectal Cancer Ascites Derived Primary Tumor Cell Cultures and Primary Tumor Tissues The DNA extraction process mentioned in the following embodiment was performed by means of a TIANGEN™ blood/tissue/cell genome extraction kit (DP304).

The library building process mentioned in the following embodiment was performed by means of an NEB DNA sequencing library building kit (E7645).

The high-throughput sequencing mentioned in the following embodiment referred to an ILLUMINA® HISEQ® X-TEN™ sequencing platform.

1. Colorectal cancer ascites samples were taken, 20 mL of a colorectal cancer ascites sample was first taken for centrifugation before in vitro culture operation to obtain an ascites cell precipitate, DNA extraction, library building and whole genome high-throughput sequencing (WGS) with a sequencing depth of 30X were performed, and the remaining colorectal cancer ascites samples were used for in vitro culture of colorectal cancer ascites primary tumor cells (the specific method refers to the previous embodiment).

2. The colorectal cancer ascites samples treated were cultured with the colorectal cancer ascites primary tumor cell medium (Table 9, where the final concentration of the human recombinant protein EGF was 20 ng/ml; the final concentration of the human recombinant protein bFGF was 20 ng/mL; the final concentration of the human recombinant protein HGF was 10 ng/ml; the final concentration of the human recombinant protein Wnt-3a was 200 ng/mL: the final concentration of the human recombinant protein Noggin was 100 ng/mL; the final concentration of the SB202190 was 10 μM; the final concentration of the A83-01 was 1 μM: the final concentration of the N-acetyl-L-cysteine was 1 mM; the final concentration of the Nicotinamide was 10 mM; the final concentration of the cortisol was 20 ng/mL; the final concentration of the Y-27632 was 10 M) for a period of time to form cell masses with a diameter of more than 80 μm, recorded as P0 generation cells, and subsequent cell masses were sequentially recorded as P1, P2, . . . , Pn according to the number of passages. $10^6$ cells were taken from each of the P1, P2, P3, P4, and P5 generations of colorectal cancer ascites derived primary tumor cell cultures for DNA extraction, library building and whole genome high-throughput sequencing (WGS) with a sequencing depth of 30X.

Figure 10:
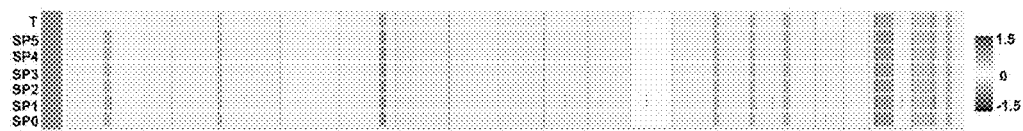
FIG. 10 shows that copy number variations of colorectal cancer ascites primary cell cultures of respective generations (P1, P2, P3, P4, P5) and cancer cells in colorectal cancer ascites are highly identical after copy number variation (CNV) analysis according to sequencing results.

3. Copy number variation (CNV) analysis was performed on each group of sequencing results to compare copy number variations between the cancer cells in the colorectal cancer ascites and the colorectal cancer ascites primary cell cultures of respective generations. As shown in FIG. 10, the copy number variations of the colorectal cancer ascites primary cell cultures of respective generations (P1, P2, P3, P4, P5) were highly consistent with the copy number variation of the cancer cells in the colorectal cancer ascites, so the colorectal cancer ascites derived primary tumor cells obtained by this method can represent the truth of cancer cells in patient's ascites.

Embodiment 27. Comparison of Success Rates of Culturing Colorectal Cancer Ascites Derived Primary Tumor Cells with Different Primary Cell Culture Media In this embodiment, the operation method and process of primary culture of all samples were completely the same (refer to the above), and only the formulas of the culture media were different. The various primary cell culture media for testing were shown in Table 36. Scheme D was the formula used in the present invention, as shown in Table 9 (where the final concentration of the human recombinant protein EGF was 40 ng/ml; the final concentration of the human recombinant protein bFGF was 20 ng/mL; the final concentration of the human recombinant protein HGF was 20 ng/mL; the final concentration of the human recombinant protein Wnt-3a was 300 ng/ml; the final concentration of the human recombinant protein Noggin was 150 ng/mL: the final concentration of the SB202190 was 10 μM; the final concentration of the A83-01 was 0.5 μM: the final concentration of the N-acetyl-L-cysteine was 1 mM: the final concentration of the Nicotinamide was 10 mM; the final concentration of the cortisol was 20 ng/ml; and the final concentration of the Y-27632 was 5 μM).

TABLE 36

Formulas of primary cell culture media for testing (100 mL)

| Culture medium | Reagent | Brand number | Amount | Final concentration |
|---|---|---|---|---|
| Scheme A | mTeSR ™ 1 medium | STEMCELL ® #05850 | 100 mL | |
| Scheme B | Alveolar Epithelial Cell Medium | SCIENCELL ® #3201 | 100 mL | |
| Scheme C | Double antibodies P/S | GIBCO ® #15140122 | 1 mL | 1% |
| | HEPES | GIBCO ® #15630080 | 1 mL | 10 mM |
| | 1,000× human recombinant protein EGF | 1,000× stock solution | 250 μL | 50 ng/ml |
| | 1,000× human recombinant protein bFGF | 1,000× stock solution | 100 μL | 20 ng/ml |
| | DMEM/F12 medium | GIBCO ® #14170161 | Made up to 100 mL | |
| Scheme D | See Table 9 | | | |

After preparation, the primary cell culture media were filtered and sterilized with a 0.22 μM syringe filter (MILLIPORE® SLGP033RS), and can be preserved at 4° C. for two weeks.

Each of the four primary cell medium schemes treated 20 colorectal cancer ascites samples. Sample treatment and culture operations were performed according to the methods described in Embodiments 18, 19, and 20. After culture for 10 days, the success rates of colorectal cancer ascites primary tumor cell culture were counted as shown in Table 37:

TABLE 37

Culture statuses of different culture media

| Primary cell medium scheme | Culture success rate |
|---|---|
| Scheme A | 5% (1/20) |
| Scheme B | 5% (1/20) |
| Scheme C | 25% (5/20) |
| Scheme D | 75% (15/20) |

It can be seen that the primary cell culture media had a great impact on the success rate of colorectal cancer ascites primary cell culture, and the colorectal cancer ascites primary tumor cell medium (Table 9) used in the present invention can stimulate the proliferation of cancer cells in the colorectal cancer ascites samples to the greatest extent and improve the success rate of colorectal cancer ascites primary tumor cell culture.

Embodiment 28. Comparison of Success Rates of Passaging Colorectal Cancer Ascites Primary Tumor Cells with Different Cell Dissociation Solutions In this embodiment, the operation method and process of primary cell passage of all samples were completely the same (refer to the above), and only the formulas of the cell dissociation solutions were different. The various cell dissociation solutions for testing were shown in Table 38. The scheme D was the formula used in the present invention, and details were shown in Table 7.

TABLE 38

Formulas of cell dissociation solutions for testing (10 mL)

| Cell dissociation solution | Reagent | Brand number | Amount | Final concentration |
|---|---|---|---|---|
| Scheme A | Trypsin | GIBCO ® #25200056 | 10 mL | |
| Scheme B | 0.5M EDTA | INVITROGEN ® #AM9261 | 10 μL | 5 mM |
| | TRYPLE ™ Express | GIBCO ® #12604013 | Made up to 10 mL | |
| Scheme C | 10× collagenase I | 10× stock solution | 1 mL | 200 U/mL |
| | 10× collagenase II | 10× stock solution | 1 mL | 200 U/mL |
| | 20× collagenase IV | 20× stock solution | 0.5 mL | 100 U/mL |
| | PBS | GIBCO ® #21-040-CVR | Made up to 10 mL | |
| Scheme D | See Table 7 | | | |

The cell dissociation solutions were prepared for current use.

20 colorectal cancer ascites samples that had been successfully cultured were selected, and the cultured colorectal cancer ascites primary tumor cells were continuously passaged with the above-mentioned four cell dissociation solutions according to the method described in Embodiment 21. When cancer cells expanded to form cell masses with a diameter of 80 μm, the cancer cells were passaged (not more than 10 times), and the maximum number of passages was recorded. The statistical results were shown in Table 39:

TABLE 39

Culture statuses of different cell dissociation solutions

| Serial number | Sample number | Scheme A | Scheme B | Scheme C | Scheme D |
|---|---|---|---|---|---|
| 1 | 20180712WSS9991 | 1 | 4 | 6 | 10 |
| 2 | 20180713LCW0205 | 0 | 2 | 5 | 9 |
| 3 | 20180717WDJ3774 | 2 | 4 | 7 | 9 |
| 4 | 20181010JJF5094 | 1 | 3 | 5 | 9 |
| 5 | 20180726ZKY6366 | 1 | 3 | 4 | 7 |
| 6 | 20180803LYB6630 | 2 | 4 | 6 | 10 |
| 7 | 20180816WC7596 | 1 | 3 | 6 | 9 |
| 8 | 20180817HX7778 | 1 | 4 | 7 | 10 |
| 9 | 20180829ZK1173 | 0 | 4 | 7 | 9 |
| 10 | 20180816FCG1697 | 0 | 2 | 7 | 10 |
| 11 | 20180815YJ3423 | 1 | 3 | 5 | 7 |
| 12 | 20180827ZXC3723 | 0 | 1 | 4 | 6 |
| 13 | 20181106SBF4195 | 1 | 2 | 4 | 7 |
| 14 | 20180904ZZC5555 | 0 | 3 | 5 | 7 |
| 15 | 20180905DP7828 | 2 | 4 | 7 | 10 |
| 16 | 20181105LXP8013 | 2 | 4 | 6 | 10 |
| 17 | 20181029JZH0836 | 0 | 0 | 2 | 6 |
| 18 | 20181031XLJ1029 | 1 | 3 | 6 | 9 |
| 19 | 20180911CZY1078 | 1 | 4 | 7 | 10 |
| 20 | 20180920SD1350 | 1 | 4 | 7 | 10 |
| Summary of possible passages | | 0-2 times | 0-4 times | 2-7 times | 6 times or more |

It can be seen that the formulas of the cell dissociation solutions had a great impact on the success rate of passage of the colorectal cancer ascites primary tumor cells. The cell dissociation solution (Table 7) used in the present invention can gently dissociate cancer cells in the cell masses, so that the samples can be continuously passaged while maintaining the activity of the colorectal cancer ascites primary tumor cells.

Embodiment 29. Culture of Colorectal Cancer Ascites Primary Tumor Cells with Cell Culture Consumables of Different Materials In this embodiment, the operation method and process of primary culture of all samples were completely the same (refer to the above), and only the materials of cell culture consumables (unmodified) were different (Table 40).

TABLE 40

Effects of unmodified culture consumables of different materials on culture of colorectal cancer ascites primary tumor cells

| Serial number | Sample number | PS | PC | PMMA | COC | COP | LAS |
|---|---|---|---|---|---|---|---|
| 1 | 20180913GW1496 | Failure | Failure | Failure | Failure | Failure | Failure |
| 2 | 20181010LTT5115 | Failure | Failure | Failure | Failure | Failure | Failure |
| 3 | 20180920CQ6010 | Failure | Failure | Failure | Failure | Failure | Success |
| 4 | 20181010CWY0293 | Success | Failure | Success | Success | Success | Success |
| 5 | 20181122WYF0822 | Failure | Failure | Success | Success | Failure | Success |
| 6 | 20181113THC1098 | Failure | Failure | Failure | Failure | Failure | Success |
| 7 | 20181012HZY1873 | Failure | Failure | Failure | Failure | Failure | Success |
| 8 | 20181022SML2256 | Success | Success | Success | Success | Failure | Success |
| 9 | 20181227ZMX2706 | Failure | Failure | Failure | Success | Success | Success |
| 10 | 20181101DHY3948 | Failure | Failure | Success | Failure | Failure | Success |
| Success rate | | 2/10 | 1/10 | 4/10 | 4/10 | 2/10 | 8/10 |

Note: Polystyrene (PS), Polycarbonate (PC), poly-methyl methacrylate (PMMA), COC resin, Cyclo Olefin Polymer (COP), low-attachment-surface (LAS).

It can be seen from Table 40 that the culture consumables of different materials had a certain impact on the success rate of colorectal cancer ascites primary tumor cell culture, and the low-attachment-surface (LAS) had the highest success rate.

Embodiment 30. Culture of Colorectal Cancer Ascites Primary Tumor Cells with CYTOP-Modified Cell Culture Consumables In this embodiment, the operation method and process of primary culture of all samples were completely the same (refer to the above), the modification methods of CYTOP™ were completely the same, and only the materials of cell culture consumables were different (Table 41).

The method of CYTOP™ modification was as follows: the cell culture vessel was first etched with pure oxygen under a power of 20 W for 3 minutes. Then, the surface of the culture dish or culture plate was covered with an appropriate amount (taking a 96-pore plank as an example, 20 μL per pore, the appropriate amount meant to completely cover the bottom of the culture dish) of a 1% CYTOP™ solution (see Table 42 for the formula), and the culture dish or culture plate can be used after the CYTOP™ solution was completely dried.

TABLE 41

Effects of CYTOP ™-modified culture consumables of different materials on culture of colorectal cancer ascites primary tumor cells

| Serial number | Sample number | PS | PC | PMMA | COC | COP | LAS |
|---|---|---|---|---|---|---|---|
| 1 | 20181022DJ4142 | Success | Success | Success | Success | Success | Success |
| 2 | 20181030FB4172 | Success | Success | Success | Success | Success | Success |
| 3 | 20181113YLS4256 | Success | Success | Success | Success | Success | Success |
| 4 | 20181101QCF4672 | Success | Success | Success | Success | Success | Success |
| 5 | 20181109YCH6089 | Failure | Failure | Failure | Failure | Failure | Failure |
| 6 | 20181130YX6531 | Success | Success | Success | Success | Success | Success |
| 7 | 20181031XYS6782 | Success | Success | Success | Success | Success | Success |
| 8 | 20181212ZWP6888 | Success | Success | Success | Success | Success | Success |
| 9 | 20181108HYX7042 | Success | Success | Success | Success | Success | Success |
| 10 | 20181109WTC7313 | Failure | Failure | Failure | Failure | Failure | Failure |
| | Success rate | 8/10 | 8/10 | 8/10 | 8/10 | 8/10 | 8/10 |

It can be seen from Table 41 that the CYTOP™ modification can effectively improve the culture success rates of various materials.

TABLE 42

1% CYTOP ™ solution (100 mL)

| Reagent | Brand number | Amount | Final concentration |
|---|---|---|---|
| CYTOP ™ | ASASHI ™ glass #CTL-809M | 1 mL | 1% |
| Fluorine oil | 3M#FC40 | Made up to 100 mL | |

The 1% CYTOP solution can be preserved for a long term at normal temperature after preparation.

Embodiment 31. Drug Sensitivity Test Using Colorectal Cancer Ascites Primary Tumor Cells The chemotherapy drugs 5-Fluorouracil, Oxaliplatin, and Irinotecan used in this embodiment were all SELLECK™ products.

The CELLTITER-GLO™ cell viability test kit mentioned in this embodiment was a PROMEGA™ product.

Figure 11:
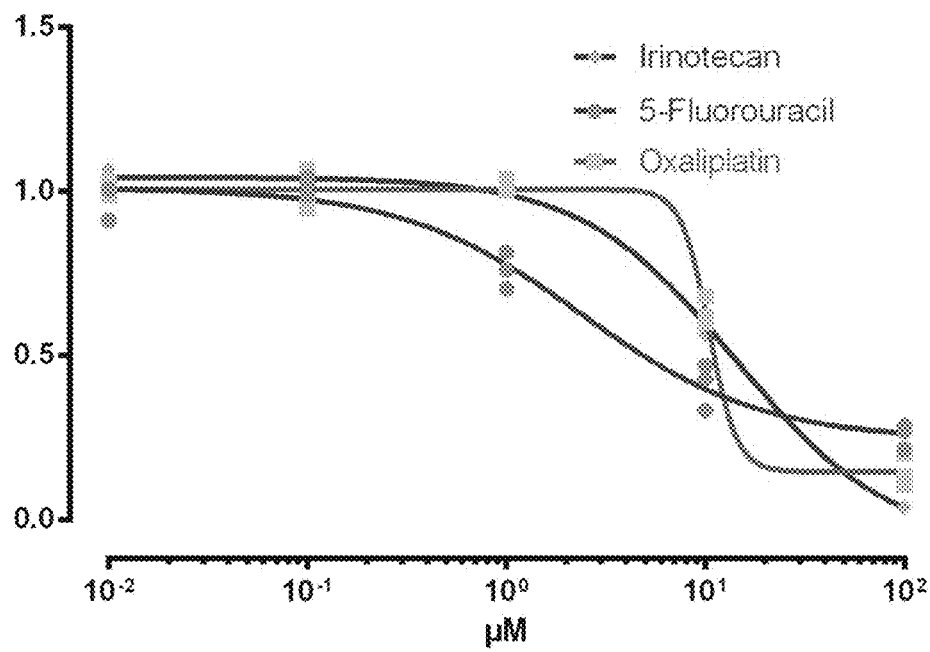
FIG. 11 shows results of in vitro drug sensitivity test using colorectal cancer ascites primary tumor cells cultured according to the present invention.

In vitro drug sensitivity test was performed using the colorectal cancer ascites primary tumor cells cultured according to the present invention: the primary cells were seeded with a density of $10^5$ cells/pore by means of a standard-sized 96-pore low-attachment cell culture plate, and 5 drug concentration gradients were provided for each drug, where n=3. After the drug was added, the cells were incubated for 7 days at 37° C. and 5% $CO_2$. After the drug action was over, the viability of the cells in each pore was tested with the CELLTITER-GLO™ cell viability test kit. The experimental results were shown in FIG. 11. The results showed that the colorectal cancer ascites primary tumor cells obtained by this method can be used for in vitro drug sensitivity test.

Embodiment 32. Microplate Chip Processing

In this embodiment, a microplate chip for culturing the colorectal cancer primary cells of the present invention was obtained by means of injection molding from a PMMA material (or a material such as PS, PC, COC, COP, or LAS). The chip can be used for colorectal cancer primary cell culture and in vitro drug sensitivity test. The design drawing of the microplate chip was shown in FIG. 12.

Figure 12:
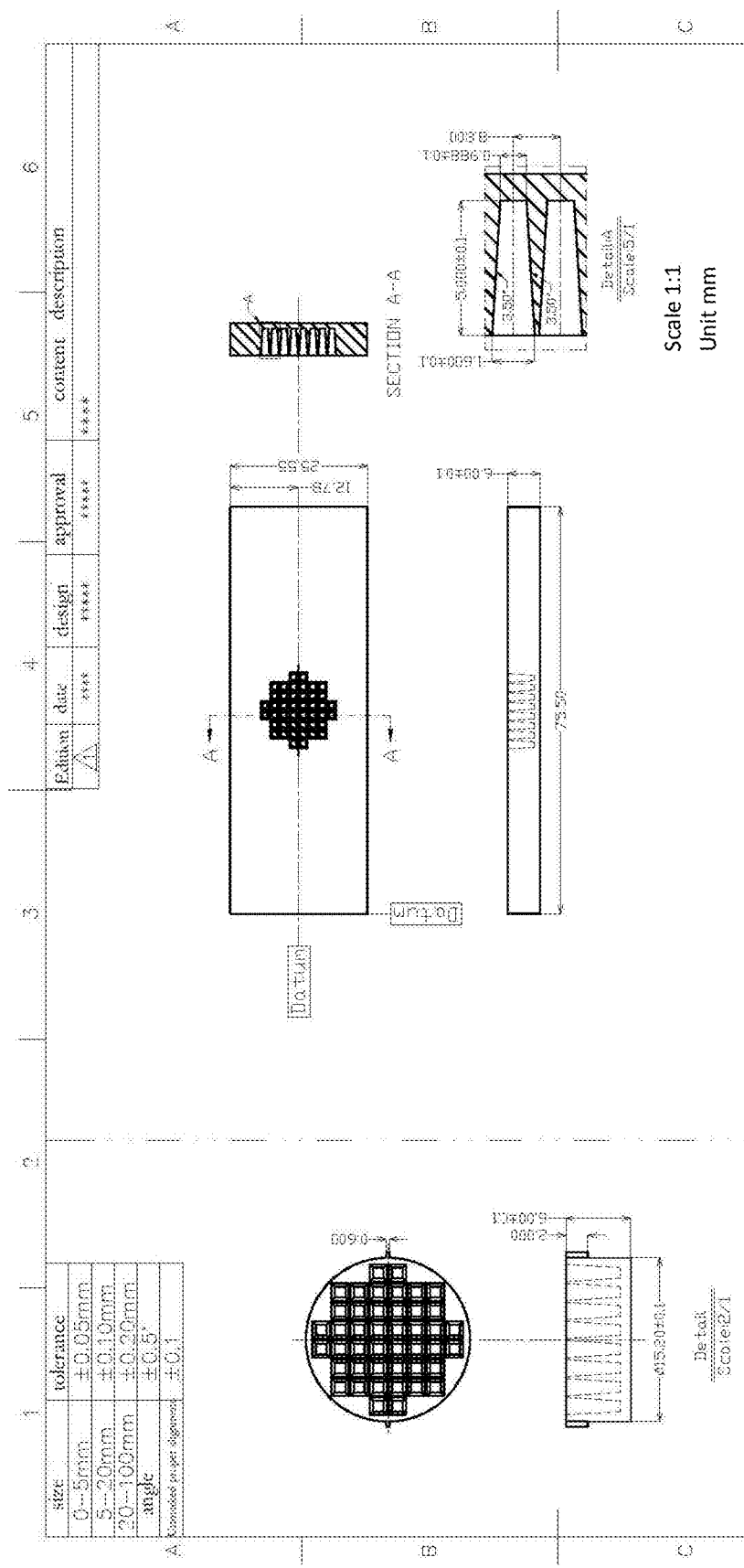
FIG. 12 is a design diagram of a microplate chip according to the present invention.

In the actual application process, the structure of the microplate chip shown in the design drawing FIG. 12 was obtained from the PMMA material (or a material such as PS, PC, COC, COP, or LAS), and then the surface of the microplate chip was modified by means of the above-mentioned CYTOP™ modification method (see Embodiment 30) to obtain the microplate chip for culturing the colorectal cancer primary cells here.

Embodiment 33. Culture of Colorectal Cancer Primary Tumor Cells from Micro Colonoscopy Puncture Samples In this embodiment, the operation method and process of primary culture of all samples were completely the same as the culture method of the colorectal cancer solid tumor primary cells (refer to the above), only the sources of the samples were different, and the samples were unified into two colonoscopy samples (Table 43).

TABLE 43

Culture statuses of colorectal cancer primary cells from colonoscopy puncture sample

| Serial number | Sample number | Culture status |
|---|---|---|
| 1 | 20181115WLF8886 | Failure |
| 2 | 20181115LWW8966 | Failure |
| 3 | 20181115ZXQ9002 | Success |
| 4 | 20181123QLP9291 | Success |
| 5 | 20181122HYJ0804 | Success |
| 6 | 20181203FFZ1845 | Success |
| 7 | 20181114LWT1950 | Success |
| 8 | 20181115MFH2041 | Success |
| 9 | 20181129LLW2643 | Success |
| 10 | 20181129YLL2937 | Success |
| Success rate | | 8/10 |

It can be seen from Table 43 that the micro samples obtained by colonoscopy puncture can still be subjected to colorectal cancer primary cell culture with a high success rate.

INDUSTRIAL APPLICATION

The present invention provides a method for extracting and culturing colorectal cancer primary tumor cells from fresh colorectal cancer solid tumor tissues or colorectal cancer ascites and supporting reagents. The method has the following advantages: for the colorectal cancer solid tumor tissues, the amount of a tissue sample is small, and only about 20 mg of colorectal cancer surgery sample is required. For the colorectal cancer ascites, samples are readily obtainable, the ascites discharged during conventional therapy of colorectal cancer patients is used to the greatest extent, and patients have no additional trauma and pain: the amount of a sample is small, and only about 50 mL of colorectal cancer ascites sample is required: the samples do not need to be immediately treated after collection, and the cell viability of more than 90% can be guaranteed after the samples isolated are treated according to this method within 72 hours. The culture cycle is short, and a $10^7$ magnitude order of colorectal cancer primary tumor cells can be obtained only within 3-10 days. The culture stability is high, and the success rates of in vitro culture of qualified colorectal cancer solid tumor and ascites samples by this method are as high as 70%-80%. The cell purity is high, and in the colorectal cancer primary cell culture obtained by this method, the proportion of cancer cells can reach 70%-95% and the interference of parenchyma cells is little. The colorectal cancer primary cell culture obtained by the method of the present invention can be used for in vitro experiments, second-generation sequencing, building of animal models, and building of cell lines at multiple cell levels. It is foreseeable that this culture method has broad application prospects in the fields of research and clinical diagnosis and treatment of colorectal cancer.

The invention claimed is:
1. A medium for culturing colorectal cancer primary cells, consisting of:
an antibacterial and antifungal agent comprising penicillin, streptomycin, and amphotericin B,
HEPES,
a glutamine supplemental solution comprising 200 mM L-alanyl-L-glutamine,
a human recombinant protein EGF,
a human recombinant protein bFGF,
a human recombinant protein HGF,
a human recombinant protein Wnt-3a,
a human recombinant protein Noggin,
SB202190,
A83-01,
an antibacterial agent for culturing primary cells comprising four antibiotics each of which targets at least one of DNA gyrase, prokaryotic ribosomal subunits, and ergosterol,
N-acetyl-L-cysteine,
Nicotinamide,
a supplemental formulation comprising insulin, transferrin, progesterone, putrescine, and selenium,
cortisol,
an embryonic neuron culture medium supplement comprising Biotin, DL Alpha Tocopherol Acetate, DL Alpha-Tocopherol, bovine serum albumin (BSA), Catalase, Human Recombinant Insulin, Human Transferrin, Superoxide Dismutase, Corticosterone, D-Galactose, Ethanolamine HCl, Glutathione (reduced), L-Carnitine HCl, Linoleic Acid, Linolenic Acid, Progesterone, Putrescine 2HCl, Sodium Selenite, and T3 (triodo-I-thyronine),
an insulin, Transferrin, selenium, ethanolamine supplement (ITS-X) comprising insulin, Transferrin, selenium, and ethanolamine,
Y-27632, and
a cell medium comprising ethanolamine, glutathione, ascorbic acid, insulin, transferrin, bovine serum albumin, and the trace elements sodium selenite, ammonium metavanadate, copper sulfate, and manganese chloride,
wherein a final concentration of the penicillin in the antibacterial and antifungal agent is 100-200 U/mL;
a final concentration of the streptomycin in the antibacterial and antifungal agent is 100-200 µg/mL;
a final concentration of the amphotericin B in the antibacterial and antifungal agent is 100-250 ng/ml;
a final concentration of the HEPES is 8-12 mM;
a final concentration of the glutamine supplemental solution is 0.8-1.2% (volume percentage);
a final concentration of the human recombinant protein EGF is 10-100 ng/ml;
a final concentration of the human recombinant protein bFGF is 10-50 ng/ml;
a final concentration of the human recombinant protein HGF is 5-25 ng/ml;
a final concentration of the human recombinant protein Wnt-3a is 200-300 ng/ml;
a final concentration of the human recombinant protein Noggin is 100-200 ng/ml;
a final concentration of the SB202190 is 5-10 µM;
a final concentration of the A83-01 is 0.25-1.25 µM;
a final concentration of the antibacterial agent for culturing primary cells is 1% (volume percentage);
a final concentration of the N-acetyl-L-cysteine is 0.5-2 mM;
a final concentration of the Nicotinamide is 5-10 mM;
a final concentration of the supplemental formulation is 1% (volume percentage);
a final concentration of the cortisol is 20-50 ng/ml;
a final concentration of the embryonic neuron culture medium supplement is 1.5-2.5% (volume percentage);

a final concentration of the ITS-X is 0.8-1.2% (volume percentage);
a final concentration of the Y-27632 is 5-20 UM; and
the remainder of the medium is the cell medium.

2. A set of reagents for culturing colorectal cancer primary cells is any of the following:
(A1) that consists of the medium according to claim 1 and any of the following additional reagents: a sample dissociation solution, a sample preservation solution, a sample washing solution, and any combinations thereof;
wherein the sample dissociation solution is composed of
a collagenase I, a collagenase II,
a collagenase IV, and
a phosphate buffered saline (PBS) solution;
wherein,
a final concentration of the collagenase I in the sample dissociation solution is 150-250 U/mL;
a final concentration of the collagenase II in the sample dissociation solution is 150-250 U/mL;
a final concentration of the collagenase IV in the sample dissociation solution is 50-150 U/mL; and
the remainder of the sample dissociation solution is the PBS; wherein the sample preservation solution is composed of
a fetal bovine serum,
a antibacterial and antifungal agent comprising a mixture of penicillin, streptomycin, and amphotericin B,
HEPES, and
HBSS;
wherein,
a final concentration of the fetal bovine serum in the sample preservation solution is 1-5% (volume percentage);
a final concentration of penicillin in the antibacterial and antifungal agent in the sample preservation solution is 100-200 U/mL;
a final concentration of streptomycin in the antibacterial and antifungal agent in the sample preservation solution is 100-200 μg/mL;
a final concentration of amphotericin B in the antibacterial and antifungal agent in the sample preservation solution is 250-500 ng/ml;
a final concentration of the HEPES in the sample preservation solution is 8-12 mM; and
the remainder of the sample preservation solution is the HBSS;
wherein the sample washing solution is composed of the antibacterial and antifungal agent and a PBS solution;
wherein,
a final concentration of penicillin in the antibacterial and antifungal agent in the sample washing solution is 100-200 U/mL;
a final concentration of streptomycin in the antibacterial and antifungal agent in the sample washing solution is 100-200 μg/mL;
a final concentration of amphotericin B in the antibacterial and antifungal agent in the sample washing solution is 250-500 ng/mL; and
the remainder of the sample washing solution is the PBS;
(A2) that consists of the medium according to claim 1 and a cell isolation buffer;
wherein the cell isolation buffer comprises
said antibacterial and antifungal agent,
heparin, and
a PBS solution; wherein,
a final concentration of the penicillin in the antibacterial and antifungal agent is 100-200 U/mL;
a final concentration of streptomycin in the antibacterial and antifungal agent is 100-200 μg/mL;
a final concentration of amphotericin B in the antibacterial and antifungal agent is 250-500 ng/ml;
a final concentration of the heparin is 10 IU/mL; and
the remainder of the cell isolation buffer is the PBS;
(A3) consists of the (A1) and any of the following reagents:
a cell dissociation solution,
a dissociation stop solution,
a cell cryopreservation solution, and any combinations thereof;
(A4) consists of the (A2) and any of the following reagents:
a cell dissociation solution,
a dissociation stop solution, and
a cell cryopreservation solution, and any combinations thereof;
wherein the composition of the cell dissociation solution is as follows:
every 10 mL of the cell dissociation solution contains 4-6 mL of a cell dissociation reagent comprising collagenolytic and proteolytic enzymes in D-PBS, and 0.5 mM EDTA,
every 10 mL of the cell dissociation solution contains 1.5-2.5 mL of an enzyme solution with Lys-C and Arg-C protease activity and comprising 200 mg/L KCl, 200 mg/L KH2PO4, 8,000 mg/L NaCl, 2,160 mg/L Na2HPO4-7H2O, 457.6 mg/L EDTA, and a recombinant protease,
wherein the final concentration of EDTA in the cell dissociation solution is 5 mM, and
the remainder of the cell isolation buffer is the PBS;
the dissociation stop solution comprises: the fetal bovine serum,
the antibacterial and antifungal agent, and
a Dulbecco's modified eagle medium (DMEM);
wherein,
a final concentration of the fetal bovine serum in the dissociation stop solution is 8-12% (volume percentage);
a final concentration of penicillin in the antibacterial and antifungal agent in the dissociation stop solution is 100-200 U/ml;
a final concentration of streptomycin in the antibacterial and antifungal agent in the dissociation stop solution is 100-200 μg/mL;
a final concentration of amphotericin B in the antibacterial and antifungal agent in the dissociation stop solution is 250-500 ng/mL; and
the remainder of the dissociation stop solution is the DMEM; the cell cryopreservation solution comprises: a cell medium comprising ethanolamine, glutathione, ascorbic acid, insulin, transferrin, bovine serum albumin, and trace elements, including sodium selenite, ammonium metavanadate, copper sulfate, and manganese chloride,
a DMSO, and
a 1% methyl cellulose solution; wherein, a volume ratio of the cell medium, the DMSO and the 1% methyl cellulose solution is 20:2:(0.8-1.2); and the 1% methyl cellulose solution is a methyl cellulose aqueous solution with a concentration of 1 g/100 ml.

3. A method for culturing colorectal cancer primary cells consisting of method A or method B:

method A: a method for culturing colorectal cancer solid tumor primary cells comprising the following steps:
(a1) dissociating colorectal cancer solid tumor tissues with a sample dissociation solution;
wherein the sample dissociation solution comprises:
a collagenase I having a final concentration of 150-250 U/mL,
a collagenase II having a final concentration of 150-250 U/mL,
a collagenase IV having a final concentration of 50-150 U/mL, and
a PBS as a remainder of the sample dissociation solution;
to obtain colorectal cancer solid tumor primary cells; and
(a2) performing suspension culture with a medium on the colorectal cancer solid tumor primary cells dissociated in (a1);
wherein the medium consists of:
an antibacterial and antifungal agent comprising penicillin, streptomycin, and amphotericin B,
HEPES,
a glutamine supplemental solution comprising 200 mM L-alanyl-L-glutamine,
a human recombinant protein EGF,
a human recombinant protein bFGF,
a human recombinant protein HGF,
a human recombinant protein Wnt-3a,
a human recombinant protein Noggin,
SB202190,
A83-01,
an antibacterial agent for culturing primary cells comprising a mixture of four antibiotics each of which targets at least one of DNA gyrase, prokaryotic ribosomal subunits, and ergosterol,
N-acetyl-L-cysteine,
Nicotinamide,
a supplemental formulation comprising insulin, transferrin, progesterone, putrescine, and selenium,
cortisol,
an embryonic neuron culture medium supplement comprising Biotin, DL Alpha Tocopherol Acetate, DL Alpha-Tocopherol, bovine serum albumin (BSA), Catalase, Human Recombinant Insulin, Human Transferrin, Superoxide Dismutase, Corticosterone, D-Galactose, Ethanolamine HCl, Glutathione (reduced), L-Carnitine HCl, Linoleic Acid, Linolenic Acid, Progesterone, Putrescine 2HCl, Sodium Selenite, and T3 (triodo-I-thyronine),
an Insulin, Transferrin, Selenium, Ethanolamine supplement solution (ITS-X),
Y-27632, and
a cell medium comprising ethanolamine, glutathione, ascorbic acid, insulin, transferrin, bovine serum albumin, and the trace elements, including sodium selenite, ammonium metavanadate, copper sulfate, and manganese chloride;
wherein
a final concentration of the penicillin in the antibacterial and antifungal agent is 100-200 U/mL;
a final concentration of the streptomycin in the antibacterial and antifungal agent is 100-200 μg/mL;
a final concentration of the amphotericin B in the ternary antibacterial and antifungal agent is 100-250 ng/ml;
a final concentration of the HEPES is 8-12 mM;
a final concentration of the glutamine supplemental solution is 0.8-1.2% (volume percentage);
a final concentration of the human recombinant protein EGF is 10-100 ng/ml;
a final concentration of the human recombinant protein bFGF is 10-50 ng/ml;
a final concentration of the human recombinant protein HGF is 5-25 ng/ml;
a final concentration of the human recombinant protein Wnt-3a is 200-300 ng/ml;
a final concentration of the human recombinant protein Noggin is 100-200 ng/ml;
a final concentration of the SB202190 is 5-10 μM;
a final concentration of the A83-01 is 0.25-1.25 UM;
a final concentration of the antibacterial agent for culturing primary cells is 1% (volume percentage);
a final concentration of the N-acetyl-L-cysteine is 0.5-2 mM;
a final concentration of the Nicotinamide is 5-10 mM;
a final concentration of the supplemental formulation is 1% (volume percentage);
a final concentration of the cortisol is 20-50 ng/ml;
a final concentration of the embryonic neuron culture medium supplement is 1.5-2.5% (volume percentage);
a final concentration of the ITS-X is 0.8-1.2% (volume percentage);
a final concentration of the Y-27632 is 5-20 M; and
the remainder of the medium is the cell medium;
method B: a method for culturing colorectal cancer ascites primary tumor cells comprises the following steps:
(b1) isolating colorectal cancer ascites primary tumor cells from colorectal cancer ascites; and
(b2) performing suspension culture with the culture medium on the colorectal cancer ascites primary tumor cells isolated in (b1).

4. The method according to claim 3, wherein in (a1), the colorectal cancer solid tumor tissues are dissociated with the sample dissociation solution,
according to a method comprising the following steps:
isolating a colorectal cancer solid tumor tissue from a patient;
cutting the isolated colorectal cancer solid tumor tissue into a plurality of tumor tissue pieces;
treating the tumor tissue pieces with the sample dissociation solution preheated at 37° C. according to an amount of 0.1-0.3 mL of the sample dissociation solution per mg of tumor tissue pieces, and
dissociating the tumor tissue pieces at 37° C. for between 15 minutes and 3 hours; or
in (b1), the colorectal cancer ascites primary tumor cells are isolated from the colorectal cancer ascites according to a method comprising the following steps:
suspending cells in the colorectal cancer ascites with a cell isolation buffer comprising an antibacterial and antifungal agent, heparin and a PBS; wherein,
a final concentration of penicillin in the antibacterial and antifungal agent is 100-200 U/mL;
a final concentration of streptomycin in the antibacterial and antifungal agent is 100-200 μg/mL;

a final concentration of amphotericin B in the antibacterial and antifungal agent is 250-500 ng/ml;
a final concentration of the heparin is 10 IU/mL; and
the remainder of the cell isolation buffer is the PBS, and
then obtaining the colorectal cancer ascites primary tumor cells by means of density gradient centrifugation.

5. The method according to claim 3, wherein in (a2), suspension culture is performed with the medium on the colorectal cancer solid tumor primary cells according to a method comprising the following steps:
performing suspension culture in a cell culture vessel with the medium on the colorectal cancer solid tumor primary cells at 37° C. and 5% $CO_2$, and
changing the medium every 2-4 days;
or in (b2), suspension culture is performed with the medium on the colorectal cancer ascites primary tumor cells according to a method comprising the following steps:
performing suspension culture in a cell culture vessel with the medium on the colorectal cancer ascites primary tumor cells at 37° C. and 5% $CO_2$, and
changing the medium every 2-4 days; and
wherein the cell culture vessel is selected from the group consisting of group (I) and group II, wherein
group (I) consists of
a cell culture vessel comprising polystyrene,
a cell culture vessel comprising polycarbonate,
a cell culture vessel comprising polymethyl methacrylate,
a cell culture vessel comprising copolymers of cycloolefin (COC) resin,
a cell culture vessel comprising cyclic olefin polymer, and
a cell culture vessel with an attachment surface that has been modified to reduce cell adhesion to the attachment surface; and
group (II) consists of a cell culture vessel selected from group (I) and modified with an amorphous fluoropolymer film to obtain a modified cell culture vessel.

6. The method according to claim 5, wherein the modified cell culture vessel is prepared by:
selecting a cell culture vessel from group (I);
etching the selected cell culture vessel with pure oxygen under a power of 20 W for 3 minutes to obtain an etched cell culture vessel;
covering a surface of the etched cell culture vessel with a 1% amorphous fluoropolymer solution; and
drying the 1% amorphous fluoropolymer solution in the air to obtain the modified cell culture vessel,
wherein the composition of the 1% amorphous fluoropolymer solution comprises: 1 ml of amorphous fluoropolymer in every 100 mL of the 1% amorphous fluoropolymer solution; and
the remainder is a fluorocarbon oil.

7. The method according to claim 4, wherein before (a1), the following steps of treating the colorectal cancer solid tumor tissues before dissociation are further comprises:
washing the surface of a colorectal cancer solid tumor tissue sample with an ethanol solution having an ethanol volume percentage of 70-75%; and
sequentially washing the colorectal cancer solid tumor tissue sample with a sample washing solution,
wherein the sample washing solution comprises an antibacterial and antifungal agent comprising:
a final concentration of penicillin in the sample washing solution of 100-200 U/mL,
a final concentration of streptomycin in the sample washing solution of 100-200 µg/mL,
a final concentration of amphotericin B in the sample washing solution of 250-500 ng/ml; and
the remainder of the sample washing solution comprising a sterile PBS solution.

8. The method according to claim 7, wherein the isolated colorectal cancer solid tumor tissues are left for no more than 2 hours before dissociation, and the tissues are preserved in a sample preservation solution comprising:
a fetal bovine serum,
an antibacterial and antifungal agent,
HEPES, and
HBSS;
wherein, a final concentration of the fetal bovine serum in the sample preservation solution is 1-5% (volume percentage);
a final concentration of penicillin in the antibacterial and antifungal agent in the sample preservation solution is 100-200 U/ml;
a final concentration of streptomycin in the antibacterial and antifungal agent in the sample preservation solution is 100-200 µg/mL;
a final concentration of amphotericin B in the antibacterial and antifungal agent in the sample preservation solution is 250-500 ng/ml;
a final concentration of the HEPES in the sample preservation solution is 8-12 mM; and
the remainder of the sample preservation solution is the HBSS, all the time prior to the treatment before dissociation.

9. The method according to claim 3, wherein in (a1), after the colorectal cancer solid tumor tissues are dissociated with the sample dissociation solution, the following steps are further comprised:
stopping the dissociation reaction with the dissociation stop solution,
collecting a cell suspension comprising the dissociated cells;
filtering the cell suspension to remove tissue debris and adherent cells;
re-suspending filtered cells with a sterile PBS solution after centrifugation;
centrifuging the re-suspended cells again, and then
re-suspending a cell precipitate formed by the second centrifugation with the medium.

10. The method according to claim 3, wherein in (a2), the following step is further comprised: when the colorectal cancer solid tumor primary cells form masses with a diameter of 50-80 µm, passaging the colorectal cancer solid tumor primary cells; and in (b2), the following step is further comprised: when the colorectal cancer ascites primary tumor cells form masses with a diameter of 50-80 µm, passaging the colorectal cancer ascites primary tumor cells.

11. The method according to claim 10, wherein a cell dissociation solution used during the passaging is the cell dissociation solution according to claim 2.

12. The method according to claim 10, wherein a dissociation stop solution used during the passaging is the dissociation stop solution according to claim 2.

13. The method according to claim 3, wherein the method further comprises a step of cryopreserving and/or thawing the colorectal cancer solid tumor primary cells or the colorectal cancer ascites primary tumor cells after 2-3 passaging expansions in a cell cryopreservation solution;

wherein the cell cryopreservation solution comprises a cell medium comprising ethanolamine, glutathione, ascorbic acid, insulin, transferrin, bovine serum albumin, and the trace elements, including sodium selenite, ammonium metavanadate, copper sulfate, and manganese chloride, a DMSO and 1% methyl cellulose solution with a concentration of 1 g cellulose per 100 ml; wherein a volume ratio of the cell medium and the DMSO and 1% methyl cellulose solution is 20:2:(0.8-1.2).

14. The method according to claim 3, wherein the colorectal cancer is a primary colorectal cancer.

15. The method according to claim 3, wherein the colorectal cancer is a colorectal cancer or colorectal cancer metastasis lesion.

16. The method according to claim 3, wherein the colorectal cancer primary cells are colorectal cancer solid tumor primary cells or colorectal cancer ascites primary tumor cells.

17. The method according to claim 3, wherein the colorectal cancer primary cells are isolated from surgical samples, colonoscopy puncture samples or ascites samples of colorectal cancer patients.

* * * * *